US006800728B2

(12) United States Patent
Schwartz

(10) Patent No.: US 6,800,728 B2
(45) Date of Patent: Oct. 5, 2004

(54) HYDRAZINE-BASED AND CARBONYL-BASED BIFUNCTIONAL CROSSLINKING REAGENTS

(75) Inventor: David A. Schwartz, Encinitas, CA (US)

(73) Assignee: Solulink Biosciences, Inc., San Diego, CA (US)

( * ) Notice: Subject to any disclaimer, the term of this patent is extended or adjusted under 35 U.S.C. 154(b) by 98 days.

(21) Appl. No.: 09/815,978

(22) Filed: Mar. 22, 2001

(65) Prior Publication Data
US 2003/0013857 A1 Jan. 16, 2003

Related U.S. Application Data
(60) Provisional application No. 60/191,186, filed on Mar. 22, 2000.

(51) Int. Cl.[7] .................. A61K 47/48; C07D 207/46; C07K 17/06; C07K 17/14; C08G 65/329
(52) U.S. Cl. ................. 530/345; 530/391.1; 530/408; 530/409; 530/810; 536/23.1; 548/542; 564/17; 564/18; 564/34; 564/37
(58) Field of Search .................. 424/179.1, 180.1, 424/181.1; 435/174, 175, 176, 177, 178, 179, 180, 181, 182; 514/2, 8, 12, 21, 44; 530/375, 391.1, 391.3, 391.5, 391.7, 391.9, 404, 405, 408, 409, 810, 811, 812, 813, 814, 815, 816; 536/23.1; 548/542; 564/17, 18, 34, 37

(56) References Cited

U.S. PATENT DOCUMENTS

| | | | |
|---|---|---|---|
| 3,808,086 A | 4/1974 | Mosimann et al. ........... 161/93 |
| 4,244,721 A | 1/1981 | Gupta et al. .................. 65/31 |
| 4,461,876 A | 7/1984 | Lieberman et al. ......... 525/374 |
| 4,707,440 A | 11/1987 | Stavrianopoulos ............. 435/6 |
| 4,775,619 A | 10/1988 | Urdea ........................... 435/6 |
| 4,874,813 A | 10/1989 | O'Shannessy ............. 525/54.1 |
| 5,118,605 A | 6/1992 | Urdea ........................... 435/6 |
| 5,151,507 A | 9/1992 | Hobbs, Jr. et al. ............ 536/23 |
| 5,206,370 A | 4/1993 | Schwartz et al. ........... 546/281 |
| 5,210,203 A | 5/1993 | Musso et al. ............... 548/130 |
| 5,329,028 A * | 7/1994 | Ashkenazi et al. ......... 548/548 |
| 5,380,833 A | 1/1995 | Urdea ....................... 536/22.1 |

(List continued on next page.)

FOREIGN PATENT DOCUMENTS

| | | |
|---|---|---|
| EP | 0280474 A2 | 8/1988 |
| EP | 0361768 A2 | 1/1990 |
| EP | 0384769 B1 | 2/1990 |
| EP | 0280474 B1 | 11/1993 |
| WO | WO-93/14779 A1 * | 8/1993 |
| WO | 9410149 | 5/1994 |
| WO | 0005208 | 2/2000 |
| WO | 0005243 | 2/2000 |
| WO | 0008042 | 2/2000 |
| WO | 0040590 | 7/2000 |
| WO | 0109385 A2 | 2/2001 |

OTHER PUBLICATIONS

Heindel et al A Novel Heterobifunctional Linker for Formyl to Thiol Coupling. Bioconjugate Chemistry. 1991, vol. 2, No. 6, pp. 427–430.*

(List continued on next page.)

Primary Examiner—Jeffrey E. Russel
(74) Attorney, Agent, or Firm—Heller, Ehrman, White & McAuliffe LLP

(57) ABSTRACT

Reagents and methods are provided for crosslinking and immobilizing biomolecules, drugs and synthetic polymers. The reagents possess (i) a thiol or amino reactive group; and (ii) a hydrazino or oxyamino moiety. Conjugates and immobilized biomolecules are also provided.

14 Claims, 9 Drawing Sheets

U.S. PATENT DOCUMENTS

| | | | |
|---|---|---|---|
| 5,420,285 A | 5/1995 | Schwartz et al. | 546/281 |
| 5,521,290 A | 5/1996 | Sivam et al. | 530/391.5 |
| 5,567,624 A | 10/1996 | Smith | 436/163 |
| 5,679,778 A | 10/1997 | Abrams et al. | 530/391.5 |
| 5,753,520 A | 5/1998 | Schwartz et al. | 436/542 |
| 5,789,576 A | 8/1998 | Daily et al. | 536/25.6 |
| 5,792,615 A | 8/1998 | Arnold et al. | 435/6 |
| 5,837,856 A | 11/1998 | Arnold, Jr. et al. | 536/24.5 |
| 5,837,860 A | 11/1998 | Anderson et al. | 536/25.3 |
| 5,854,410 A | 12/1998 | Arnold, Jr. et al. | 536/23.1 |
| 5,856,571 A | 1/1999 | Berninger et al. | 564/37 |
| 5,877,220 A | 3/1999 | Schwartz et al. | 514/626 |
| 5,880,270 A | 3/1999 | Berninger et al. | 530/391.1 |
| 5,900,481 A | 5/1999 | Lough et al. | 536/55.3 |
| 5,919,758 A * | 7/1999 | Sytkowski | 514/8 |
| 5,955,597 A | 9/1999 | Arnold, Jr. et al. | 536/24.3 |
| 5,958,901 A | 9/1999 | Dwyer et al. | 514/75 |
| 6,001,826 A | 12/1999 | Murrer et al. | 514/183 |
| 6,020,526 A | 2/2000 | Schwartz et al. | 564/153 |
| 6,028,188 A | 2/2000 | Arnold, Jr. et al. | 536/25.3 |
| 6,034,135 A | 3/2000 | Schwartz et al. | 514/616 |
| 6,133,436 A | 10/2000 | Köster et al. | 536/24.3 |
| 6,217,845 B1 | 4/2001 | Schwartz et al. | 424/1.69 |
| 6,238,860 B1 * | 5/2001 | Whelihan | 435/5 |

OTHER PUBLICATIONS

Zara et al. A Carbohydrate–Directed Heterobifunctional Cross–Linking Reagent for the Synthesis of Immunoconjugates. Analytical Biochemistry. 1991, vol. 194, pp. 156–162.*

Scott et al. Synthesis Of Reagents For The One Step Incorporation Of Hydrazide Functionality . . . Bioorganic & Medicinal Chemistry Letters. 1996, vol. 6, No. 13, pp. 1491–1496.*

Abrams et al., "Technetium–99m–Human Polyclonal IgG Radiolabeled via the Hydrazino Nicotinamide Derivative for Imaging Focal Sites of Infection in Rats", *J. Nucl. Med., 31(12)*:2022–2028; (1990).

Agrawal, S. (Ed.), *Methods in Molecular Biology.20*, Book: Protocols for Oligonucleotides and Analogs, Synthesis and Properties, Humana Press, (1993), pp. ix–xi.

Bischoff et al., "Introduction of 5'–Terminal Functional Groups into Synthetic Oligonucleotides for Selective Immobilization", *Anal. Biochem., 164*:336–344; (1987).

Bridger et al., "A Comparison of Cleavable and Noncleavable Hydrazinopyridine Linkers for the $^{99m}$Tc Labeling of Fab' Monoclonal Antibody Fragments", *Bioconj. Chem., 7*:255–264; (1996).

Change et al., "Early Results in the International Design of New Bifunctional Chelators", *6th Conference on Radioimmunodetection and Radioimmunotherapy of Cancer—Supplement to Cancer, 80*:2347–2353; (1997).

Ellis et al., "Development and Clinical Uses of Haemphilus b Conjugate Vaccines", Book: *Marcel Dekker, Inc.; New York;* (1994) pp. xi–xiii.

Ghosh et al., "Covalent attachment of oligonucleotides to solid supports", *Nucl. Acids. Res., 15(3)*:5353–5372; (1987).

Ghosh et al., "Synthesis of 5'–Oligonucleotide Hydrazide Derivatives and Their Use in Preparation of Enzyme–Nucleic Acid Hybridization Probes", *Anal. Biochem., 178*:43–51; (1989).

Greene et al., "Protective Groups in Organic Synthesis", Book: 2nd Edition, *John Wiley & Sons, Inc.* pp. ix–x.

Hermanson et al., *Bioconjugate Techniques:* Academic Press, 1996, pp. vii–xxiii.

Hostomsky et al., "Solid–phase assembly of DNA duplexes from synthetic oligonucleotides," *Nucl. Acid. Symp. Ser., 18*:241–244; (1987).

IUPAC–IUB: "IUPAC–IUB Commission on Biochemical Nomenclature Abbreviated Nomenclature of Synthetic Polypeptides (Polymerized Amino Acids)", *Biochem., 11(5)*:942–944; (1972).

Kaneko et al., "New Hydrazone Derivatives of Adriamycin and Their Immunoconjugates—a Correlation between Acid Stability and Cytotoxicity," *Bioconj. Chem., 2(3)*:133–141; (1991).

King et al., "Preparation of Protein Conjugates via Intermolecular Hydrazone Linkage", *Biochem., 25*:5774–5779; (1986).

Marble et al., "RNA Transcription from Immobilized DNA Templates," *Biotechnol. Prog. 11*:393–396; (1995).

Reynolds et al., "Antisense oligonucleotides containing an internal non–nucleotide–based linker promote site–specific cleavage of RNA", *Nucl. Acids. Res., 24(4)*:760–765; (1996).

Reynolds et al., "Synthesis and thermodynamics of oligonucleotides containing chirally pure Rp methylphosphonate linkages", *Nucl. Acids. Res. 24(22)*:4584–4591; (1996).

Rose et al., "Natural Peptides as Building Blocks for the Synthesis of Large Protein–like Molecules with Hydrazone and Oxime Linkages", *Bioconjugate Chem., 7*:552–556; (1996).

Salo et al., "Aminooxy Functionalized Oligonucleotides: Preparation, On–Support Derivatization, and Postsynthetic Attachment to Polymer Support", *Bioconjugate Chem., 10*:815–823; (1999).

Schwartz et al., "Preparation of Hydrazino–Modified Proteins and Their Use for the Synthesis of 99mTc–Protein Conjugates," *Bioconjugate Chem., 2*:333–336; (1991).

Timofeev et al., "Regioselective immobilization of short oligonucleotides to acrylic copolymer gels", *Nucl. Acids. Res., 24(6)*:3142–3148; (1996).

Trevisiol et al., "The Oxyamino–Aldehyde Coupling Reaction: An Efficient Method for the Derivatization of Oligonucleotides", *Tetrahedron Lett, 38(50)*:8687–8690; (1997).

Trevisiol et al., "Synthesis of Nucleoside Triphosphate that Contain an Aminooxy Function for 'Post–Ampification Labeling'", *Eur. J. Org. Chem.,* pp. 211–217; (2000).

* cited by examiner

Preparation of 5'-aromatic aldehyde-modified oligonucleotide:

Preparation of 5'-heteroaromatic hydrazine-modified oligonucleotide:

Conjugation of hydrazino-modified oligonucleotide to aldehyde-modified oligonucleotide

SEQUENCE LISTING

<160> NUMBER OF SEQ ID NOS: 1

<210> SEQ ID NO 1
<211> LENGTH: 26
<212> TYPE: DNA
<213> ORGANISM: Artificial Sequence
<220> FEATURE:
<223> OTHER INFORMATION: 25-mer phosphodiester oligonucleotide modified
      to incorporate a C6-aminolinker
<221> NAME/KEY: modified_base
<222> LOCATION: 1
<223> OTHER INFORMATION: N= n-hexylamino linker

<400> SEQUENCE: 1 nttttttag cctaactgat gccatg                                          26

US 6,800,728 B2

HYDRAZINE-BASED AND CARBONYL-BASED BIFUNCTIONAL CROSSLINKING REAGENTS

RELATED APPLICATIONS

Benefit of priority under 35 U.S.C. §119(e) is claimed to U.S. provisional patent application No. 60/191,186, filed Mar. 22, 2000, to Schwartz, entitled "NOVEL HYDRAZINE-BASED AND CARBONYL-BASED BIFUNCTIONAL CROSSLINKING REAGENTS." The disclosure of the above-referenced application is incorporated herein in its entirety.

FIELD OF THE INVENTION

The present disclosure may be applied in general to the field of chemistry, more particularly in the area of crosslinking reagents.

BACKGROUND OF THE INVENTION

Methods to crosslink biomolecules such as proteins, oligonucleotides and carbohydrates to each other, to radioactive and non-radioactive metal chelates, to drugs and to surfaces have allowed development of both in vitro and in vivo diagnostic assays as well as in vivo therapies. A wide variety of methods have been developed and reviewed (Greg T. Hermanson, Bioconjugate Techniques, Academic Press).

There are a limited number of crosslinking couples, i.e., maleimide/thiol and bromoacetamide/thiol, that are routinely used to prepare conjugates for diagnostic and therapeutic uses. These reagents have limitations in that at high protein concentrations (i.e., >5 mg/mL) protein/protein crosslinking may occur. Also, the maleimido-modified moieties have a limited half-life due to hydrolysis at neutral and basic pH. Incorporation of thiol moieties on biomolecules requires both a coupling and a subsequent activation step. The resultant thiol-modified proteins can readily oxidize to form disulfide polymerized proteins. Also macromolecules containing disulfide bonds, i.e., antibodies, are readily cleaved following activation of the thiol moiety by a reductant. Also, quantitation of the maleimido moiety is somewhat difficult and there is no means to quantify directly the level of conjugation. Therefore, it is advantageous to have a crosslinking couple that does not have these limitations.

Consequently there is a need for crosslinking couples that: bind more efficiently to surfaces; may be controlled to achieve desired crosslinking; do not lead to homobifunctional crosslinking following modification of aggregated proteins; are stable to biological conditions of varying pH and temperature; are stable in solution or when lyophilized; are one step modifications unlike those reagents currently used in the art, e.g., SATA, SPDP type reagents; can be indirectly quantified by a spectrophotometric assay; and can be used to quantify the level of conjugation by spectrophotometric means utilizing the bond formed following conjugation.

Therefore, it is an object herein to provide reagents and methods for crosslinking biomolecules to other biomolecules, polymers, metals or drugs that meet the above needs and have improved properties over known crosslinking reagents and methods.

SUMMARY OF THE INVENTION

Reagents and methods for crosslinking biomolecules to other biomolecules, polymers, metals or drugs are provided. The reagents are heterobifunctional compounds possessing, as one of the functionalities a hydrazino group, a carbonyl group, or an oxyamino group, all as defined herein. The reagents are used in the methods provided herein to afford improved crosslinking for both in vitro and in vivo diagnostic assays as well as in vivo therapies.

Provided herein are bifunctional compounds containing amine or thiol reactive moieties and a hydrazino or oxyamino moiety that may be utilized to modify small molecules, macromolecules, biomolecules and solid surfaces. A number of hydrazino moieties may be utilized including aliphatic and aromatic hydrazine derivatives, including, but not limited to, hydrazines, hydrazides, semicarbazides, carbazides, thiosemicarbazides, thiocarbazides, hydrazine carboxylates and carbonic acid hydrazines (see, e.g., FIG. 1).

In one embodiment, the reagents for use in the methods provided herein have the formula:

or a derivative thereof, where B is an amino or thiol reactive moiety; Y is a hydrazino group, as defined herein, an oxyamino group or a carbonyl group; and R is a divalent group having any combination of the following groups, which are combined in any order: arylene, heteroarylene, cycloalkylene, $C(R^{10})_2$, —$C(R^{10})$=$C(R^{10})$—, >C=$C(R^{12})(R^{13})$, >$C(R^{12})(R^{13})$, —C≡C—, O, $S(G)_a$, $P(J)_b(R^{10})$, $P(J)_b(LR^{10})$, $N(R^{10})$, >$N^+(R^{12})(R^{13})$ and $C(L)$; where a is 0, 1 or 2; b is 0, 1, 2 or 3; G is O or $NR^{10}$; J is S or O; and L is S, O or $NR^{10}$; each $R^{10}$ is a monovalent group independently selected from hydrogen and $M^1$—$R^{14}$; each $M^1$ is a divalent group independently having any combination of the following groups, which groups are combined in any order: a direct link, arylene, heteroarylene, cycloalkylene, $C(R^{15})_2$, —$C(R^{15})$=$C(R^{15})$—, >C=$C(R^{12})(R^{13})$, >$C(R^{12})(R^{13})$, —C≡C—, O, $S(G^1)_a$, $P(J)_b(R^{15})$, $P(J)_b(LR^{15})$, $N(R^{15})$, $N(COR^{15})$, >$N^+(R^{12})(R^{13})$ and $C(L)$; where a is 0, 1 or 2; b is 0, 1, 2 or 3; $G^1$ is O or $NR^{15}$; J is S or O; and L is S, O or $NR^{15}$; $R^{14}$ and $R^{15}$ are each independently selected from the group among hydrogen, halo, pseudohalo, cyano, azido, nitro, $SiR^{16}R^{17}R^{18}$, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^{19}R^{20}$; $R^{19}$ and $R^{20}$ are each independently selected from hydrogen, alkyl, alkenyl, alkynyl, cycloalkyl, aryl, aralkyl, heteroaryl, heteroaralkyl and heterocyclyl; $R^{12}$ and $R^{13}$ are selected from (i) or (ii) as follows: (i) $R^{12}$ and $R^{13}$ are independently selected from among hydrogen, alkyl, alkenyl, alkynyl, cycloalkyl, aryl and heteroaryl; or (ii) $R^{12}$ and $R^{13}$ together form alkylene, alkenylene or cycloalkylene; $R^{16}$, $R^{17}$ and $R^{18}$ are each independently a monovalent group selected from hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^{19}R^{20}$; and $R^{11}$, $R^{12}$, $R^{13}$, $R^{14}$, $R^{15}$, $R^{16}$, $R^{17}$, $R^{18}$, $R^{19}$ and $R^{20}$ can be substituted with one or more substituents each independently selected from Z, wherein Z is selected from alkyl, alkenyl, alkynyl, aryl, cycloalkyl, cycloalkenyl, hydroxy, $S(O)_nR^{30}$, $NR^{30}R^{31}$, $COOR^{30}$, $COR^{30}$, $CONR^{30}R^{31}$, $OC(O)NR^{30}R^{31}$, $N(R^{30})C(O)R^{31}$, alkoxy, aryloxy, heteroaryl, heterocyclyl, heteroaryloxy, heterocyclyloxy, aralkyl, aralkenyl, aralkynyl, heteroaralkyl, heteroaralkenyl, heteroaralkynyl, aralkoxy, heteroaralkoxy, alkoxycarbonyl, carbamoyl, thiocarbamoyl, alkoxycarbonyl, carboxyaryl, halo, pseudohalo, haloalkyl and carboxamide; h is 0, 1 or 2; and $R^{30}$ and $R^{31}$ are each independently selected from among hydrogen, halo, pseudohalo, cyano, azido, nitro, trialkylsilyl, dialkylarylsilyl, alkyldiarylsilyl, triarylsilyl, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy, amino, amido, alkylamino, dialkylamino, alkylarylamino, diarylamino and arylamino.

Thus, the reagents provided herein are aliphatic and aromatic crosslinking compounds that possess (i) a thiol or amine reactive group; and (ii) a hydrazino, oxyamino or carbonyl group. Thiol reactive groups are moieties that react directly with sulfhydryl groups forming stable thioether bonds. These thiol reactive groups include, but are not limted to, maleimido, α-bromoacetamido and pyridyldisulfides. Amino reactive moieties are those that react directly with amine moieties forming amide bonds. These amino reactive groups include, but are not limited to, N-hydroxysuccinimidyl, p-nitrophenyl, pentafluorophenyl and N-hydroxybenzotriazolyl esters.

Hydrazino groups, as defined herein, include, but are not limited to, hydrazines, hydrazides, semicarbazides, carbazides, thiosemicarbazides, thiocarbazides, hydrazine carboxylates and carbonic acid hydrazines (see, e.g., FIG. 1). Oxyamino groups have the formula R—O—NH$_2$.

In certain embodiments herein, R is an aliphatic divalent group. In these embodiments, R is a divalent group having any combination of the following groups, which are combined in any order: cycloalkylene, $C(R^{10})_2$, —$C(R^{10})$=C ($R^{10}$)—, >C=C($R^{12}$)($R^{13}$), >C($R^{12}$)($R^{13}$), —C≡C—, O, $S(G)_a$, $P(J)_b(R^{10})$, $P(J)_b(LR^{10})$, $N(R^{10})$, >$N^+(R^{12})(R^{13})$ and C(L); where the variables are as defined above.

In other embodiments herein, Y is a hydrazino group, as defined herein. In further embodiments, Y is selected from semicarbazido, thiosemicarbazido, oxyamino, carbazido or thiocarbazido. In another embodiment, R is not $(CH_2)_n$, where n is 1–12. In a further embodiment, Y is oxyamino.

Modified biomolecules are provided. These compounds are prepared by reaction of a biomolecule of interest with one of the functionalities of a bifunctional reagent, as described herein. The modified biomolecules are available for conjugation or immobilization using the remaining functional group. Biomolecules for use herein include, but are not limited to, proteins including antibodies, glycoproteins, peptides, oligonucleotides, RNA and DNA.

Conjugate vaccines are also provided. The conjugates are formed from a protein carrier, which is modified by reaction with a bifunctional reagent, as described herein. Conjugation of the resulting hydrazino or oxyamino modified protein with, e.g., a bacterial polysaccharide, that has been oxidized to produce aldehyde groups, produces a conjugate vaccine. The bifunctional reagents for use in these embodiments are, in certain embodiments, those where R is an aliphatic group.

Also provided herein are modified solid supports, including, but not limited to, synthetic polymers, beads, glass, slides, metals and particles that have been modified by reaction with a bifunctional reagent provided herein to afford modified synthetic polymers, beads, latex, glass, slides, metals, including colloidal metals, and particles that possess a hydrazino or oxyamino group. These modified solid supports are useful in immobilization of biomolecules that possess or are modified to possess a carbonyl group. The immobilized biomolecules may be used in diagnostic and therapeutic applications.

DETAILED DESCRIPTION OF PREFERRED EMBODIMENTS

Definitions

Unless defined otherwise, all technical and scientific terms used herein have the same meaning as is commonly understood by one of skill in the art to which this invention belongs. All patents, patent applications and publications referred to throughout the disclosure herein are incorporated by reference in their entirety. In the event that there are a plurality of definitions for a term herein, those in this section prevail.

Figure 1:
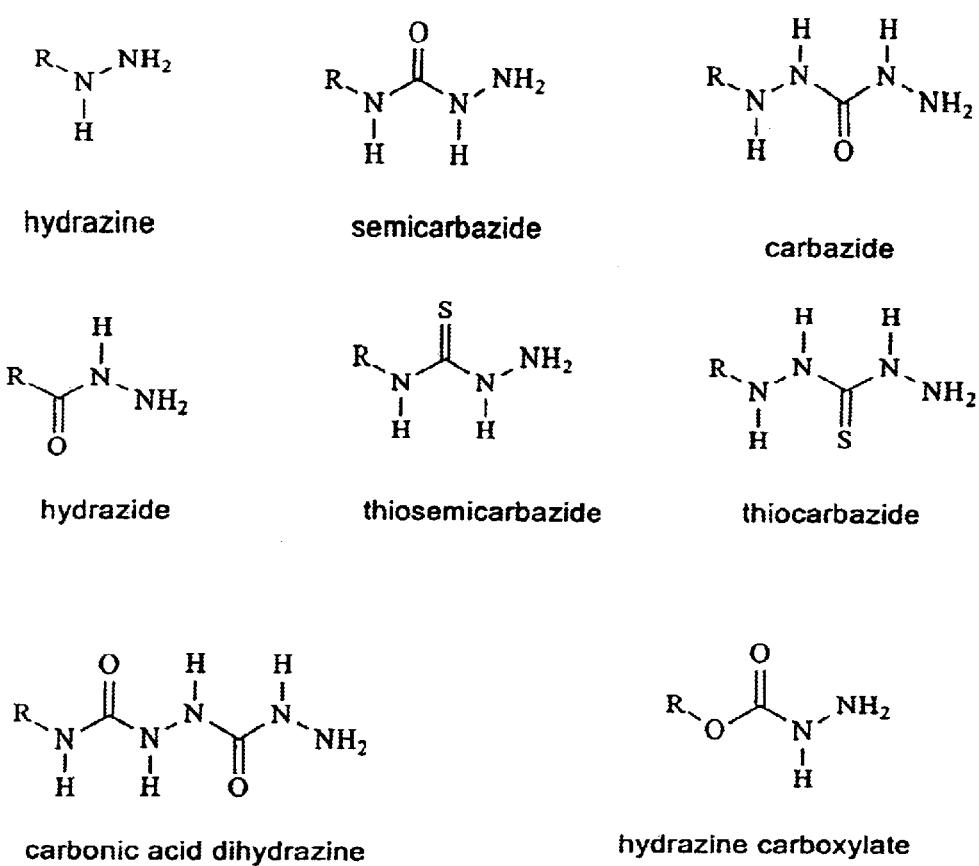
FIG. 1 illustrates structures of hydrazino derivatives provided herein.

As used herein, "hydrazino groups" include, but are not limited to, hydrazines, hydrazides, semicarbazides, carbazides, thiosemicarbazides, thiocarbazides, hydrazine carboxylates and carbonic acid hydrazines (see, e.g., FIG. 1).

As used herein, hydrazone linkages (R—NHN=C(R)(R)) include, but are not limited to, hydrazones, acyl hydrazones, semicarbazones, carbazones, thiosemicarbazones, thiocarbazones, hydrazine carboxylates and carbonic acid hydrazones.

As used herein, an oxyamino group has the formula —O—NH$_2$. An oxime has the formula —O—N=R.

As used herein, a protected hydrazino or a protected oxyamino group refers to a hydrazino or oxyamino group that has been derivatized as a salt of the hydrazino or oxyamino group, including but not limited to, mineral acids salts, such as but not limited to hydrochlorides and sulfates, and salts of organic acids, such as but not limited to acetates, lactates, malates, tartrates, citrates, ascorbates, succinates, butyrates, valerates and fumarates; or with any amino or hydrazino protecting group known to those of skill in the art (see, e.g., Greene et at. (1999) Protective Groups in Organic Synthesis (3rd Ed.) (J. Wiley Sons, Inc.)). Preferred amino and hydrazino protecting groups herein include, but are not limited to, amino or hydrazino protecting groups useful in the synthesis of oligonucleotides, more preferably monomethoxytrityl (MMT). dimethoxytrityl (DMT), trimethoxytrityl (TMT), 9-fluorenylmethoxy-carbonyl (FMOC), acetyl, trifluoroacetyl, benzoyl, or a hydrazone or oxime that is cleaved under mild acidic conditions (e.g., 100 mM acetate or 100 mM morpholino-N-ethylsulfonic acid (MES), pH 4.5–5.5) including, but not limited to, a hydrazone or oxime formed from a lower aliphatic aldehyde or ketone, preferably from acetone, propanal, cyclohexanone or 2-butanone.

As used herein, "—COOSu" refers to an N-hydroxysuccinimidyl ester.

As used herein, an oligonucleotide is a nucleic acid, including, but not limited to, a ribonucleic acid (RNA), a deoxyribonucleic acid (DNA), and analogs thereof such as a protein nucleic acid (PNA), of any length, including chromosomes and genomic material, such as PCR products or sequencing reaction products, preferably DNA including double and single stranded forms. Single stranded forms of the oligonucleotides are also provided.

As used herein, a conjugate is a compound containing two components covalently linked together. For example, a first component, e.g., a protein, is conjugated through a covalent hydrazone linkage to a second component, e.g. a second protein as defined herein, to form a conjugate.

As used herein, carbonyl derivatives include, but are not limited to, ketones and aldehydes.

As used herein, complementary reactive groups are those that, when reacted together, form a covalent linkage, including, but not limited to, a hydrazone or oxime linkage. Thus, a hydrazino group, as defined herein, is complementary to a carbonyl derivative. An oxyamino group is also complementary to a carbonyl derivative.

As used herein, a biopolymer is any compound found in nature, or derivatives thereof, made up of monomeric units. Biopolymers include, but are not limited to, oligonucleotides, RNA, DNA, peptides, peptide nucleic acids (PNAs), proteins including antibodies, glycoproteins and oligosaccharides. Thus, the monomeric units include, but are not limited to, nucleotides, nucleosides, amino acids, PNA monomers, monosaccharides, and derivatives thereof.

As used herein, a macromolecule refers to a molecule of colloidal size (i.e., of high molecular weight), including, but not limited to, proteins, polynucleic acids, polysaccharides and carbohydrates.

As used herein, a reporter molecule refers to a molecule, such as an enzyme or indicator, which is capable of generating a detectable signal (e.g., by calorimetric, chemiluminescent, bioluminescent, fluorescent, or potentiometric means) when contacted with a suitable substrate under appropriate reaction conditions. Exemplary reporter enzymes include, but are not limited to, alkaline phosphatase, horseradish peroxidase, β-galactosidase, aryl esterase, sulfatase and urease.

As used herein, a nucleobase is a heterocyclic moiety that is found in naturally occurring oligonucleotides, including ribonucleic acids (RNA) and deoxyribonucleic acids (DNA), and analogs thereof, including deaza analogs. Preferred nucleobases include, but are not limited to, cytosines, uracils, adenines, guanines and thymines, and analogs thereof including deaza analogs.

As used herein, a fluorophore refers to a fluorescent compound. Fluorescence is a physical process in which light is emitted from the compound following absorption of radiation. Generally, the emitted light is of lower energy and longer wavelength than that absorbed. Preferred fluorophores herein are those whose fluorescence can be detected using standard techniques.

As used herein, a derivative of a compound includes a salt, ester, enol ether, enol ester, solvate or hydrate thereof that can be prepared by those of skill in this art using known methods for such derivatization. Salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl) aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Enol ethers include, but are not limited to, derivatives of formula C=C(OR) where R is hydrogen, alkyl, alkenyl, alkynyl, aryl, heteroaryl, aralkyl, heteroaralkyl, cycloalkyl ar heterocyclyl. Enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl ar heterocyclyl. Solvates and hydrates are complexes of a compound with one or more solvent or water molecule, preferably 1 to about 100, more preferably 1 to about 10, most preferably one to about 2, 3 or 4, solvent or water molecules.

It is to be understood that the compounds provided herein can contain chiral centers. Such chiral centers can be of either the (R) or (S) configuration, or can be a mixture thereof. Thus, the compounds provided herein may be enantiomerically pure, or be stereoisomeric or diastereomeric mixtures. In the case of amino acid residues, such residues may be of either the L or D form. The preferred configuration for naturally occurring amino acid residues is L.

As used herein alkyl, alkenyl and alkynyl carbon chains, if not specified, contain from 1 to 20 carbons, preferably 1 to 16 carbons, and are straight or branched. Alkenyl carbon chains of from 2 to 20 carbons preferably contain 1 to 8 double bonds, and the alkenyl carbon chains of 1 to 16 carbons preferably contain 1 to 5 double bonds. Alkynyl carbon chains of from 2 to 20 carbons preferably contain 1 to 8 triple bonds, and the alkynyl carbon chains of 2 to 16 carbons preferably contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyltyl and isohexyl. The alkyl, alkenyl and alkynyl groups, unless otherwise specified, can be optionally substituted, with one or more groups, preferably alkyl group substituents that can be the same or different. As used herein, lower alkyl, lower alkenyl, and lower alkynyl refer to carbon chains having less than about 6 carbons. As used herein, "alk(en)(yn)yl" refers to an alkyl group containing at least one double bond and at least one triple bond.

As used herein, an "alkyl group substituent" includes halo, haloalkyl, preferably halo lower alkyl, aryl, hydroxy, alkoxy, aryloxy, alkyloxy, alkylthio, arylthio, aralkyloxy, aralkylthio, carboxy alkoxycarbonyl, oxo and cycloalkyl.

As used herein, "aryl" refers to cyclic groups containing from 5 to 19 carbon atoms. Aryl groups include, but are not limited to groups, such as fluorenyl, substituted fluorenyl, phenyl, substituted phenyl, naphthyl and substituted naphthyl, in which the substituent is lower alkyl, halogen, or lower alkoxy.

As used herein, an "aryl group substituent" includes alkyl, cycloalkyl, cycloalkylalkyl, aryl, heteroaryl optionally substituted with 1 or more, preferably 1 to 3, substituents selected from halo, halo, alkyl and alkyl, aralkyl, heteroaralkyl, alkenyl containing 1 to 2 double bonds, alkynyl containing 1 to 2 triple bonds, alk(en)(yn)yl groups, halo, pseudohalo, cyano, hydroxy, haloalkyl and polyhaloalkyl, preferably halo lower alkyl, especially trifluoromethyl, formyl, alkylcarbonyl, arylcarbonyl that is optionally substituted with 1 or more, preferably 1 to 3, substituents selected from halo, haloalkyl and alkyl, heteroarylcarbonyl, carboxy, alkoxycarbonyl, aryloxycarbonyl, aminocarbonyl, alkylaminocarbonyl, dialkylaminocarbonyl, arylaminocarbonyl, diarylaminocarbonyl, aralkylaminocarbonyl, alkoxy, aryloxy, perfluoroalkoxy, alkenyloxy, alkynyloxy, arylalkoxy, aminoalkyl, alkylaminoalkyl, dialkylaminoalkyl, arylaminoalkyl, amino, alkylamino, dialkylamino, arylamino, alkylarylamino, alkylcarbonylamino, arylcarbonylamino, azido, nitro, mercapto, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl and arylaminosulfonyl.

As used herein, "aralkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "cycloalkyl" refers to a saturated mono- or multicyclic ring system, preferably of 3 to 10 carbon atoms, more preferably 3 to 6 carbon atoms; cycloalkenyl and cycloalkynyl refer to mono- or multicyclic ring systems that respectively include at least one double bond and at least one triple bond. Cycloalkenyl and cycloalkynyl groups can preferably contain 3 to 10 carbon atoms, with cycloalkenyl groups more preferably containing 4 to 7 carbon atoms and cycloalkynyl groups more preferably containing 8 to 10 carbon atoms. The ring systems of the cycloalkyl, cycloalkenyl and cycloalkynyl groups can be composed of one ring or two or more rings which can be joined together in a fused, bridged or spiro-connected fashion, and can be optionally substituted with one or more alkyl group substituents. "Cycloalk(en)(yn)yl" refers to a cylcoalkyl group containing at least one double bond and at least one triple bond.

As used herein, "heteroaryl" refers to a monocyclic or multicyclic ring system, preferably of about 5 to about 15 members where one or more, more preferably 1 to 3 of the atoms in the ring system is a heteroatom, that is, an element other than carbon, for example, nitrogen, oxygen and sulfur atoms. The heteroaryl can be optionally substituted with one or more, preferably 1 to 3 aryl group substituents. The heteroaryl group can be optionally fused to a benzene ring. Exemplary heteroaryl groups include, for example, furyl, imidazolyl, pyrrolidinyl, pyrimidinyl, tetrazolyl, thienyl, pyridyl, pyrrolyl, N-methylpyrrolyl, quinolinyl and isoquinolinyl, with pyridyl and quinolinyl being preferred.

As used herein, "heterocyclic" refers to a monocyclic or multicyclic ring system, preferably of 3 to 10 members, more preferably 4 to 7 members, even more preferably 5 to 6 members, where one or more, preferably 1 to 3 of the atoms in the ring system is a heteroatom, that is, an element other than carbon, for example, nitrogen, oxygen and sulfur atoms. The heterocycle can be optionally substituted with one or more, preferably 1 to 3 aryl group substituents. Preferred substituents of the heterocyclic group include hydroxy, amino, alkoxy containing 1 to 4 carbon atoms, halo lower alkyl, including trihalomethyl, such as trifluoromethyl, and halogen. As used herein, the term heterocycle includes reference to heteroaryl.

As used herein, the nomenclature alkyl, alkoxy, carbonyl, etc. are used as is generally understood by those of skill in this art. For example, as used herein alkyl refers to saturated carbon chains that contain one or more carbons; the chains are straight or branched or include cyclic portions or be cyclic.

As used herein, alicyclic refers to aryl groups that are cyclic.

For purposes herein, where the number of any given substituent is not specified (e.g., "haloalkyl"), there can be one or more substituents present. For example, "haloalkyl" includes one or more of the same or different halogens. As another example, "$C_{1-3}$alkoxyphenyl" can include one or more of the same or different alkoxy groups containing one, two or three carbons.

As used herein, "halogen" or "halide" refers to F, Cl, Br or I.

As used herein, pseudohalides are compounds that behave substantially similar to halides. Such compounds can be used in the same manner and treated in the same manner as halides ($X^-$, in which X is a halogen, such as Cl or Br). Pseudohalides include, but are not limited to, cyanide, cyanate, thiocyanate, selenocyanate, trifluoromethoxy, trifluoromethyl and azide.

As used herein, "haloalkyl" refers to a lower alkyl radical in which one or more of the hydrogen atoms are replaced by halogen including, but not limited to, chloromethyl, trifluoromethyl, 1-chloro-2-fluoroethyl and the like.

As used herein, "haloalkoxy" refers to RO— in which R is a haloalkyl group.

As used herein, "sulfinyl" or "thionyl" refers to —S(O)—. As used herein, "sulfonyl" or "sulfuryl" refers to —S(O)$_2$—. As used herein, "sulfo" refers to —S(O)$_3$—.

As used herein, "carboxy" refers to a divalent radical, —C(O)O—.

As used herein, "aminocarbonyl" refers to —C(O)NH$_2$.

As used herein, "alkylaminocarbonyl" refers to —C(O) NHR in which R is hydrogen or alkyl, preferably lower alkyl. As used herein "dialkylaminocarbonyl" as used herein refers to —C(O)NR'R in which R' and R are independently selected from hydrogen or alkyl, preferably lower alkyl; "carboxamide" refers to groups of formula —NR'COR.

As used herein, "diarylaminocarbonyl" refers to —C(O) NRR' in which R and R' are independently selected from aryl, preferably lower aryl, more preferably phenyl.

As used herein, "aralkylaminocarbonyl" refers to —C(O)NRR' in which one of R and R' is aryl, preferably lower aryl, more preferably phenyl, and the other of R and R' is alkyl, preferably lower alkyl.

As used herein, "arylaminocarbonyl" refers to —C(O)NHR in which R is aryl, preferably lower aryl, more preferably phenyl.

As used herein, "alkoxycarbonyl" refers to —C(O)OR in which R is alkyl, preferably lower alkyl.

As used herein, "aryloxycarbonyl" refers to —C(O)OR in which R is aryl, preferably lower aryl, more preferably phenyl.

As used herein, "alkoxy" and "alkylthio" refer to RO— and RS—, in which R is alkyl, preferably lower alkyl.

As used herein, "aryloxy" and "arylthio" refer to RO— and RS—, in which R is aryl, preferably lower aryl, more preferably phenyl.

As used herein, "alkylene" refers to a straight, branched or cyclic, preferably straight or branched, divalent aliphatic hydrocarbon group, preferably having from 1 to about 20 carbon atoms, more preferably 1 to 12 carbons, even more preferably lower alkylene. The alkylene group is optionally substituted with one or more "alkyl group substituents." There can be optionally inserted along the alkylene group one or more oxygen, sulphur or substituted or unsubstituted nitrogen atoms, where the nitrogen substituent is alkyl as previously described. Exemplary alkylene groups include methylene (—CH$_2$—), ethylene (—CH$_2$CH$_2$—), propylene (—(CH$_2$)$_3$—), cyclohexylene (—C$_6$H$_{10}$—), methylenedioxy (—O—CH$_2$—O—) and ethylenedioxy (—O—(CH$_2$)$_2$—O—). The term "lower alkylene" refers to alkylene groups having 1 to 6 carbons. Preferred alkylene groups are lower alkylene, with alkylene of 1 to 3 carbon atoms being particularly preferred.

As used herein, "alkenylene" refers to a straight, branched or cyclic, preferably straight or branched, divalent aliphatic hydrocarbon group, preferably having from 2 to about 20 carbon atoms and at least one double bond, more preferably 1 to 12 carbons, even more preferably lower alkenylene. The alkenylene group is optionally substituted with one or more "alkyl group substituents." There can be optionally inserted along the alkenylene group one or more oxygen, sulphur or substituted or unsubstituted nitrogen atoms, where the nitrogen substituent is alkyl as previously described. Exemplary alkenylene groups include —CH=CH—CH=CH— and —CH=CH—CH$_2$—. The term "lower alkenylene" refers to alkenylene groups having 2 to 6 carbons. Preferred alkenylene groups are lower alkenylene, with alkenylene of 3 to 4 carbon atoms being particularly preferred.

As used herein, "alkynylene" refers to a straight, branched or cyclic, preferably straight or branched, divalent aliphatic hydrocarbon group, preferably having from 2 to about 20 carbon atoms and at least one triple bond, more preferably 1 to 12 carbons, even more preferably lower alkynylene. The alkynylene group is optionally substituted with one or more "alkyl group substituents." There can be optionally inserted along the alkynylene group one or more oxygen, sulphur or substituted or unsubstituted nitrogen atoms, where the nitrogen substituent is alkyl as previously described. Exemplary alkynylene groups include —C≡C—C≡C—, —C≡C— and —C≡C—CH$_2$—. The term "lower alkynylene" refers to alkynylene groups having 2 to 6 carbons. Preferred alkynylene groups are lower alkynylene, with alkynylene of 3 to 4 carbon atoms being particularly preferred.

As used herein, "alk(en)(yn)ylene" refers to a straight, branched or cyclic, preferably straight or branched, divalent aliphatic hydrocarbon group, preferably having from 2 to about 20 carbon atoms and at least one triple bond, and at least one double bond; more preferably 1 to 12 carbons, even more preferably lower alk(en)(yn)ylene. The alk(en)(yn)ylene group is optionally substituted with one or more "alkyl group substituents." There can be optionally inserted along the alkynylene group one or more oxygen, sulphur or substituted or unsubstituted nitrogen atoms, where the nitrogen substituent is alkyl as previously described. Exemplary alk(en)(yn)ylene groups include —C=C—(CH$_2$)$_n$—C≡C—, where n is 1 or 2. The term "lower alk(en)(yn)ylene" refers to alk(en)(yn)ylene groups having up to 6 carbons. Preferred alk(en)(yn)ylene groups are lower alk(en)(yn)ylene, with alk(en)(yn)ylene of 4 carbon atoms being particularly preferred.

As used herein, "arylene" refers to a monocyclic or polycyclic, preferably monocyclic, divalent aromatic group, preferably having from 5 to about 20 carbon atoms and at least one aromatic ring, more preferably 5 to 12 carbons, even more preferably lower arylene. The arylene group is optionally substituted with one or more "alkyl group substituents." There can be optionally inserted around the arylene group one or more oxygen, sulphur or substituted or unsubstituted nitrogen atoms, where the nitrogen substituent is alkyl as previously described. Exemplary arylene groups include 1,2-, 1,3- and 1,4-phenylene. The term "lower arylene" refers to arylene groups having 5 or 6 carbons. Preferred arylene groups are lower arylene.

As used herein, "heteroarylene" refers to a divalent monocyclic or multicyclic ring system, preferably of about 5 to about 15 members where one or more, more preferably 1 to 3 of the atoms in the ring system is a heteroatom, that is, an element other than carbon, for example, nitrogen, oxygen and sulfur atoms. The heteroarylene group are optionally substituted with one or more, preferably 1 to 3, aryl group substituents.

As used herein, "alkylidene" refers to a divalent group, such as =CR'R'', which is attached to one atom of another group, forming a double bond. Exemplary alkylidene groups are methylidene (=CH$_2$) and ethylidene (=CHCH$_3$). As used herein, "aralkylidene" refers to an alkylidene group in which either R' or R'' is and aryl group.

As used herein, "amido" refers to the divalent group —C(O)NH—. "Thioamido" refers to the divalent group —C(S)NH—. "Oxyamido" refers to the divalent group —OC(O)NH—. "Thiaamido" refers to the divalent group —SC(O)NH—. "Dithiaamido" refers to the divalent group —SC(S)NH—. "Ureido" refers to the divalent group —HNC(O)NH—. "Thioureido" refers to the divalent group —HNC(S)NH—.

As used herein, "semicarbazide" refers to —NHC(O)NHNH—. "Carbazate" refers to the divalent group —OC(O)NHNH—. "Isothiocarbazate" refers to the divalent group —SC(O)NHNH—. "Thiocarbazate" refers to the divalent group —OC(S)NHNH—. "Sulfonylhydrazide" refers to the group —SO$_2$NHNH—. "Azo" refers to the divalent group —N=N—. "Hydrazinyl" refers to the divalent group —NH—NH—.

As used herein, the term "amino acid" refers to a-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid.

As used herein, when any particular group, such as phenyl or pyridyl, is specified, this means that the group is unsubstituted or is substituted. Preferred substituents where not specified are halo, halo lower alkyl, and lower alkyl.

As used herein, a composition refers to any mixture of two or more products or compounds. It can be a solution, a suspension, liquid, powder, a paste, aqueous, non-aqueous or any combination thereof.

As used herein, a combination refers to any association between two or more items.

As used herein, fluid refers to any composition that can flow. Fluids thus encompass compositions that are in the form of semi-solids, pastes, solutions, aqueous mixtures, gels, lotions, creams and other such compositions.

As used herein, substantially identical to a product means sufficiently similar so that the property of interest is sufficiently unchanged so that the substantially identical product can be used in place of the product.

The term "amino reactive group" refers to moieties that react directly with amine moieties forming amide bonds. These amino reactive groups include, but are not limited to, N-hydroxysuccinimidyl, p-nitrophenyl, pentafluorophenyl and N-hydroxybenzotriazolyl esters.

The term "thiol reactive group" refers to moieties that react directly with sulfhydryl groups forming stable sulfide bonds. These thiol reactive groups include, but are not limted to, maleimido, α-bromoacetamido and pyridyldisulfides.

The term "ethyleneoxide moiety" or "PEG" or "PEO" refers to polymers formed from repeating —CH$_2$CH$_2$O— moieties.

The term "saturated or unsaturated carbocyclic moiety" refers to carbon containing ring structures of 3–20 carbons possessing up to 10 unsaturated bonds.

The term "hydrazine derivatives" refers to moieties possessing N—N bonds including, but not limited to, hydrazines, hydrazides, carbazides, thiocarbazides, semicarbazides, and thiosemicarbazides.

The term "oligonucleotide" refers to any nucleic acid molecule of 2–2000 nucleosides in length. The oligonucleotide may be composed of naturally occurring nucleosides adenosine, guanosine, cytidine, thymidine and uridine, modified nucleosides or a combination of naturally occurring and modified nucleosides. The nucleosides may be joined by naturally occurring phosphodiester linkages or modified linkages including for example phosphorothioate linkages, methylphosphonate linkages and peptide backbones (peptide nucleic acids (PNA)).

The term "carbonyl moiety" refers to moieties possessing an aldehyde (RCHO) or a ketone (RCOR).

The term "natural molecule" refers to a biologically derived molecule including for example proteins, peptides, oligonucleotides, carbohydrates and lipids.

The term "synthetic molecule" refers to a small molecule or polymer that is not naturally derived.

As used herein, the abbreviations for any protective groups, amino acids and other compounds, are, unless indicated otherwise, in accord with their common usage, recognized abbreviations, or the IUPAC-IUB Commission on Biochemical Nomenclature (see, *Biochem.* 1972, 11, 942).

A. Heterobifunctional Crosslinking Reagents

Provided herein are bifunctional molecules (reagents) possessing (i) electrophilic groups, including, but not limited to, thiol- and amino-reactive groups, including, but not limited to, maleimido, α-bromoacetamido, pyridyldisulfides, N-hydroxysuccinimidyl ester, p-nitrophenyl ester, pentafluorophenyl ester and N-hydroxybenzotriazolyl ester; and (ii) protected nucleophilic moieties, including, but not limted to, hydrazino and oxyamino groups. In one embodiment, methods to incorporate these bifuncutional on biomolecules and surfaces are provided. Further methods provide conjugates formed from the reaction of (i) a hydrazine or oxyamino modified molecule, biomolecule or surface; and (ii) a molecule, biomolecule or surface possessing a carbonyl moiety, or a molecule, biomolecule or surface prepared to possess a carbonyl moiety.

The reagents are bifunctional molecules containing a first reactive component that forms a covalent bond with a complementary reactive component on a biomolecule or surface, as well as a hydrazine or oxyamino group that is protected such that it will not react with the first component on the bifunctional molecule and will be readily removed following incorporation on the biomolecule or surface.

The reagents provided herein are broadly applicable to a variety of molecules, biomolecules and surfaces. Methods known in the art describe hydrazine-(see, e.g., Rose et al. (1996) *Bioconjugate Chem.* 7:552), hydrazide-(see, e.g., King et al. (1986) *Biochemistry* 25:5774), and oxyamino- (see, e.g., Salo et al. (1999) *Bioconjugate Chem.* 10:815) substituted biomolecules, and their reaction with aldehyde modified biomolecules and surfaces. In methods known in the art, the functionalities were incorporated in a means idiosyncratic to that use. There are no known methods that can be broadly used to form biomolecule/biomolecule conjugates or immobilize biomolecules on hydrazine or oxyamino surfaces.

Kaneko et al. (1991) *Bioconj. Chem.* 2:133 describes the preparation of pyridyldisulfide-substituted hydrazone derivative crosslinkers. This paper identified acid-labile bonds for crosslinking of adriamycin to monoclonal antibodies and release of the adriamycin following localization and internalization of the drug/protein conjugate. It was demonstrated that the hydrazone formed from hydrazides, an acyl hydrazine, was the optimal bond for this purpose. In testing various hydrazine (NHNH$_2$) (see, e.g., FIG. 1) derivatives, they found that hydrazones formed from aromatic hydrazines, aliphatic semicarbazides and aliphatic thiosemicarbazides were unsuitable for their purposes as the hydrazones were completely stable to acidic conditions.

Previously, Schwartz et al. (U.S. Pat. Nos. 5,206,370, 5,420,285, 5,753,520, and European Patent Specification No. EP 0 384 769 B1) described the synthesis and protein-modifying properties of a series of aromatic hydrazides, hydrazines and thiosemicarbazides. The hydrazine and thiosemibarbazide-modified conjugates were used to bind metals, e.g., technetium and rhenium, to macromolecules for use in diagnosis and treatment of diseases. This work was further described in Abrams et al. (1990) *J. Nucl. Med.* 31:2022 and Schwartz et al. (1991) *Bioconj. Chem.* 2:333. However, these references do not describe the construction or use of the reagents described therein as bifunctional crosslinking reagents to carbonyl, i.e., aldehyde or ketone, modified biomolecules, polymers or solid surfaces.

1. Aliphatic Hydrazine-based Bifunctional Modification Reagents

Provided herein are aliphatic bifunctional crosslinking reagents of formula I:

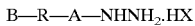

or a derivative thereof, where A is —NH(C=O)—, —NH(C=S)—, —NHNH(C=O)—, —NHNH(C=S)—, or a direct bond to R; B is an amino or thiol reactive moiety; and R is an aliphatic divalent group having any combination of the following groups, which are combined in any order: cycloalkylene, $C(R^{10})_2$, —$C(R^{10})$=$C(R^{10})$—, >C=$C(R^{12})(R^{13})$, >$C(R^{12})(R^{13})$, —C≡C—, O, $S(G)_a$, $P(J)_b(R^{10})$, $P(J)_b(LR^{10})$, $N(R^{10})$, >$N^+(R^{12})(R^{13})$ and C(L); where the variables are as defined above; and X is a negative counterion, including halide, pseudohalide, sulfate, phosphate, boronate, an organic carboxylate, including, but not limited to, trifluoroacetate, and the anion of an inorganic acid. In certain embodiments, R is, or is a combination of, a saturated straight or branched chain of 2 to 20 carbon atoms, a chain of 2 to 2000 ethyleneoxide moieties, and a saturated or unsaturated carbocyclic moiety of 3 to 20 carbon atoms.

In these embodiments, the reagents are stable isolatable derivatives of molecules that possess two cross-reactive moieties including but not limited to, an amine or thiol reactive moiety and a hydrazine-derived moiety.

In certain embodiments, the reagents include:

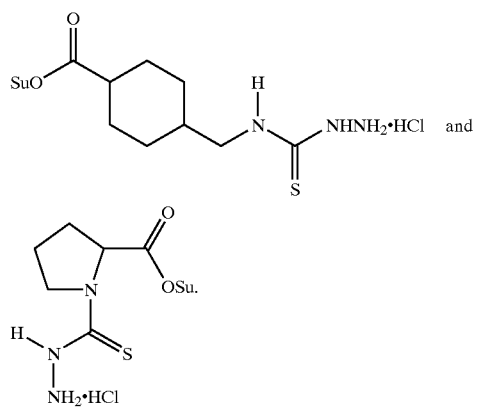

In other embodiments, the aliphatic bifunctional reagents are hydrazino compounds where the hydrazino group is protected as a hydrazone. In these embodiments, the reagents have formula II:

B—R—A—NHN=CR¹R²    II or a derivative thereof, where A is NH(C=O)—, NHNH(C=O)—, NH(C=S)—or NHNH(C=S)—or a direct bond to R; B is an amino or thiol reactive moiety; R is an aliphatic divalent group having any combination of the following groups, which are combined in any order: cycloalkylene, $C(R^{10})_2$, —$C(R^{10})$=$C(R^{10})$—, >C=$C(R^{12})(R^{13})$, >$C(R^{12})(R^{13})$, —C≡C—, O, $S(G)_a$, $P(J)_b(R^{10})$, $P(J)_b(LR^{10})$, $N(R^{10})$, >$N^+(R^{12})(R^{13})$ and C(L); where the variables are as defined above; $R^1$ is a saturated straight chain of 3 to 20 carbon atoms, a chain of 2 to 2000 ethyleneoxide moieties, or a saturated or unsaturated carbocyclic moiety of 3 to 20 carbon atoms; and $R^2$ is a saturated straight chain of 3 to 20 carbon atoms, a chain of 2 to 2000 ethyleneoxide moieties, or a saturated or unsaturated carbocyclic moiety of 3 to 20 carbon atoms. In certain embodiments, R is, or is a combination of, a saturated straight chain of 3 to 20 carbon atoms, a chain of 2 to 2000 ethyleneoxide moieties, and a saturated or unsaturated carbocyclic moiety of 3 to 20 carbon atoms.

In certain of these embodiments, the reagents include:

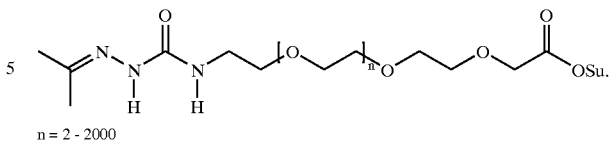

n = 2 - 2000

In one embodiment, the reagents provided herein are hydrazides of formula III:

B—R—(C=O)—NHNH₂.HX    III or a derivative thereof, where B is an amino or thiol reactive moiety; R is an aliphatic divalent group having any combination of the following groups, which are combined in any order: cycloalkylene, $C(R^{10})_2$, —$C(R^{10})$=$C(R^{10})$—, >C=$C(R^{12})(R^{13})$, >$C(R^{12})(R^{13})$, —C≡C—, O, $S(G)_a$, $P(J)_b(R^{10})$, $P(J)_b(LR^{10})$, $N(R^{10})$, >$N^+(R^{12})(R^{13})$ and C(L); where the variables are as defined above; and X is a negative counterion, including halide, pseudohalide, sulfate, phosphate, boronate, an organic carboxylate, including, but not limited to, trifluoroacetate, and the anion of an inorganic acid. In certain embodiments, R is, or is a combination of, a saturated straight chain of 3 to 20 carbon atoms, a chain of 2 to 2000 ethyleneoxide moieties or a saturated or unsaturated carbocyclic moiety of 3 to 20 carbon atoms.

In another embodiment, aliphatic bifunctional hydrazide reagents are provided. These reagents include a cleavable bond for further manipulation. Cleavable bonds include, but are not limited to, acid cleavable, photocleavable and disulfide bonds.

The use of cleavable linkers for both in vitro and in vivo applications has been described. In Kaneko et al. (1994) *Bioconjugate Chem.* 2:133, a hydrazone formed from an aliphatic hydrazide was successfully employed to deliver an adriamycin/antibody conjugate to a tumor wherein the drug was released following endocytosis and lowering of the pH in the endosome to 5. Disulfide linkages which are cleaved following treatment with reducing agents such as thiols have been successfully used to isolate receptors following covalent linking between a ligand and a receptor. Reagents such as SAED (sulfosuccinimidyl 2-(7-azido-4-methylcoumarin-3-acetamido)ethyl-1,3'-dithiopropionate; Pierce Chemicals, Rockford, Ill.) and SASD (Sulfosuccinimidyl 2-(p-azidosalicylamido)ethyl-1,3'-dithiopropionate) have been used.

In another embodiment, the bifunctional hydrazide reagents provided herein form acid cleavable hydrazones. These reagents are advantageous as the can be used to modify biomolecules or carriers such as polymers in a single step. These modified aliphatic hydrazide biomolecules or carriers can subsequently react with carbonyl containing biomolecules, drug or other therapeutic or diagnostic reagent to readily form a hydrazone that can be cleaved following exposure to mild aqueous acid conditions at pH<5.

In a further embodiment, solid supports such as beads, chromatographic supports or surfaces are modified with these aliphatic hydrazide reagents for similar purposes. The reagents described herein are preferable to the two step method described by King et al. ((1986) *Biochemistry* 25:5774) to incorporate aliphatic hydrazides. The reagents described herein are further preferable as disulfide reducing agents such as dithiothreitol which reduce native disulfide bonds in proteins are not used. Thus the use of these reagents will retain the native structure of the protein. This is especially important when an antibody is one component of a conjugate as its native structure is dependent on disulfide bridges.

In these embodiments, the reagents include:

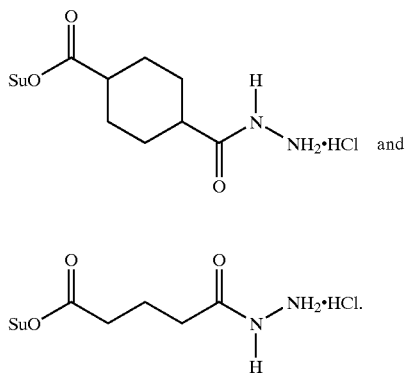

2. Aromatic and Heteroaromatic Hydrazine-based Bifunctional Modification Reagents Also intended for use in the methods provided herein are aromatic and heteroaromatic hydrazine-based bifunctional modification reagents such as those described in U.S. Pat. Nos. 5,206,370, 5,420,285 and 5,753,520, and European Patent Specification No. EP 0 384 769 B1. The disclosures of these references are incorporated herein by reference in their entirety. In particular, the reagents have formulae IV, V or VI:

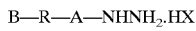 

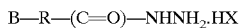 

or derivatives thereof, where B, A, $R^1$ and $R^2$ are as defined above, and R is an aromatic, polyaromatic or heteroaromatic moiety, or combinations thereof.

In other embodiments, the reagents have formula IVa:

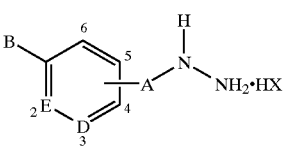

or a derivative thereof, where A is NH(C=O), NH(C=S), NH(C=NH), NHNH(C=O), NHNH(C=S), NHNH(C=NH) or a direct bond; B is an amino or thiol reactive group; D is a carbon or nitrogen atom; E is a carbon or nitrogen atom; and X is a negative counter ion, oxygen, sulfur or —NH.

In another embodiment, the reagents have formula Va:

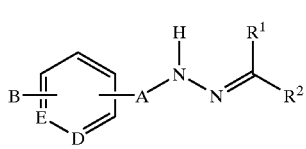

or a derivative thereof, where A is NH(C=O), NH(C=S), NH(C=NH), NHNH(C—O), NHNH(C=S), NHNH(C=NH) or a direct bond; B is an amino or thiol reactive group; D is a carbon or nitrogen atom; E is a carbon or nitrogen atom; $R^1$ is hydrogen or a saturated straight chain of 1 to 12 carbon atoms; and $R^2$ is hydrogen or a saturated straight chain of 1 to 12 carbon atoms.

In a further embodiment, the reagents have formula VIa:

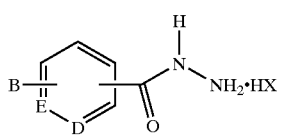

or a derivative thereof, where B is an amino or thiol reactive group; D is a carbon or nitrogen atom; E is a carbon or nitrogen atom; and X is a negative counter ion, oxygen, sulfur or —NH.

In certain embodiments, the reagents include:

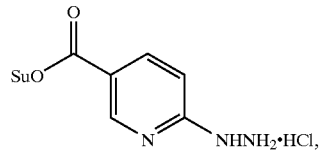

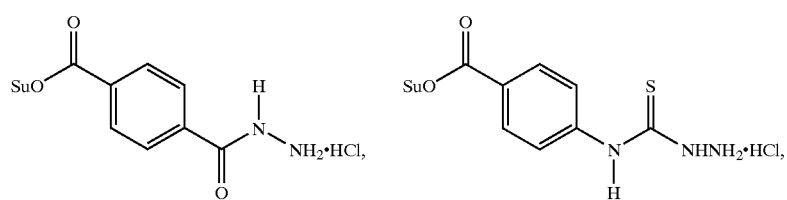

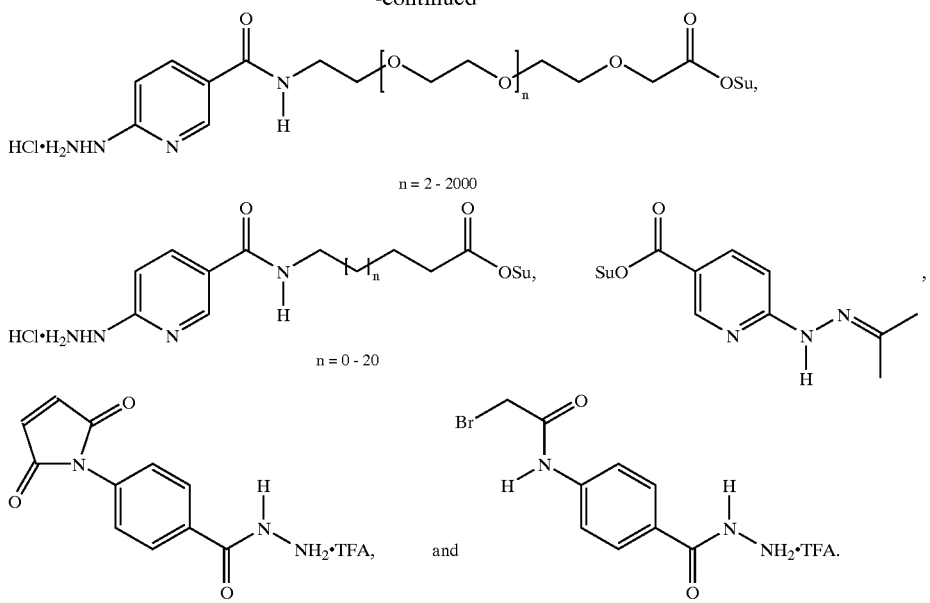

n = 2 - 2000 n = 0 - 20

3. Oxyamino Derivatives

In another embodiment, the bifunctional reagents for use in the methods provided herein have formulae VII or VIII:

$$B—R—ONH_2 \cdot HX \quad \quad \text{VII}$$

or $$B—R—ON=C(R^1R^2) \quad \quad \text{VIII}$$

where R is an aliphatic divalent group having any combination of the following groups, which are combined in any order: cycloalkylene, $C(R^{10})_2$, $—C(R^{10})=C(R^{10})—$, $>C=C(R^{12})(R^{13})$, $>C(R^{12})(R^{13})$, $—C\equiv C—$, O, $S(G)_a$, $P(J)_b(R^{10})$, $P(J)_b(LR^{10})$, $N(R^{10})$, $>N^+(R^{12})(R^{13})$ and C(L); where the variables are as defined above; B is an amino or thiol reactive moiety; $R^1$ is H or a saturated straight chain of 3 to 20 carbon atoms, a chain of 2 to 2000 ethyleneoxide moieties, or a saturated or unsaturated carbocyclic moiety of 3 to 20 carbon atoms; $R^2$ is a saturated straight chain of 3 to 20 carbon atoms, a chain of 2 to 2000 ethyleneoxide moieties, or a saturated or unsaturated carbocyclic moiety of 3 to 20 carbon atoms; and X is a negative counterion, including halide, pseudohalide, sulfate, phosphate, boronate, an organic carboxylate, including, but not limited to, trifluoroacetate, and the anion of an inorganic acid. In certain embodiments herein, R is a straight chain, branched or cyclic aliphatic moiety, a aromatic, heteroaromatic, polyaromatic or polyheteroaromatic moiety, a saturated straight chain of 2 to 20 carbon atoms, a chain of 2 to 2000 ethyleneoxide moieties, or a saturated or unsaturated carbocyclic moiety of 3 to 20 carbon atoms, or a combination thereof.

In certain embodiments, the reagents include:

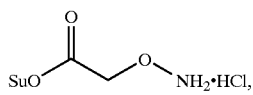

-continued

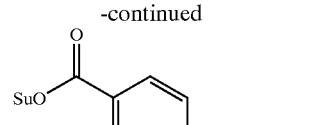

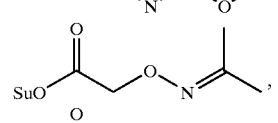

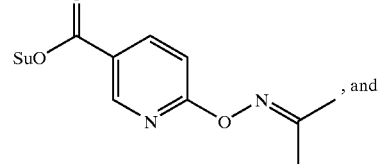

, and

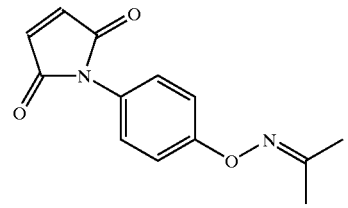

4. Bifunctional Carbonyl Reagents

In other embodiments, the hydrazine modified first component of a conjugation reaction is reacted with a second component of the conjugation reaction that has been modified to possess a carbonyl moiety by use of a bifunctional carbonyl reagent of formula IX:

$$B—R—C(=O)W \quad \quad \text{IX}$$

or a derivative thereof, where W is H or a straight, branched or cyclic aliphatic carbon chain of 1–20 atoms, or an aromatic or heteroaromatic group; B is an amino or thiol reactive moiety; and R is an aliphatic divalent group having any combination of the following groups, which are combined in any order: cycloalkylene, $C(R^{10})_2$, $—C(R^{10})=C(R^{10})—$, $>C=C(R^{12})(R^{13})$, $>C(R^{12})(R^{13})$, $—C\equiv C—$, O, $S(G)_a$, $P(J)_b(R^{10})$, $P(J)_b(LR^{10})$, $N(R^{10})$, $>N^+(R^{12})(R^{13})$ and $C(L)$; where the variables are as defined above. In certain embodiments herein, R is a straight, branched or cyclic aliphatic carbon chain of 1–20 atoms, or a aromatic or heteroaromatic group.

B. Modified Biomolecules

In a further embodiment, the bifunctional hydrazino and oxyamino molecules described herein are reacted with biomolecules, polymers or appropriately modified surfaces to modify the these molecules to incorporate one or more hydrazino or oxyamino moiety. The electrophilic moiety of these bifunctional molecules, i.e., the amino or thiol reactive moieties, of the bifunctional reagents react with nucleophilic groups on biomolecules, including, but not limited to, the terminal amino group of lysine on proteins, thereby incorporating the hydrazino or oxyamino function. These amino or thiol reactive moieties may also react with synthetic biomolecules such as oligonucleotides or peptides modified to incorporate the nucleophilic moiety, e.g., hydrazine or oxyamino. It will be appreciated by those of skill in the art that biomolecules such as proteins that contain multiple amino groups, i.e., lysines, may be reacted with many mole equivalents of bifunctional modification reagents to convert as many lysines as desired to modified lysines. The degree of modification can be controlled by the addition of the number of mole equivalents of modification reagent added to the protein.

In another embodiment, the bifunctional hydrazino and oxyamino reagents provided herein may be used directly during solid phase syntheses of biomolecules, including, but not limited to, peptides or oligonucleotides. This is in contrast to maleimido or α-bromoacetamido succinimidyl ester bifunctional reagents which are unstable to conditions employed to cleave and/or deprotect the synthetic biomolecules.

1. Proteins

In one embodiment, proteins modified with hydrazino and oxyamino moieties by reaction of bifunctional hydrazino and oxyamino reagents provided herein are provided. These modified proteins are prepared in a single step reaction by addition of the bifunctional hydrazino or oxyamino compounds to the protein in suitably buffered solutions, i.e., pH 7–9. Following incubation of the reaction for 1–4 hours, the excess reagent is removed by size exclusion gel filtration to provide the hydrazino or oxyamino modified protein.

2. Oligonucleotides

In a further embodiment, synthetic oligonucleotides prepared to incorporate amino groups either 3', 5' or internally using methods and reagents well known to those of skill in the art (see, e.g., Glen Research Corporation, Sterling, Va.) are reacted with the bifunctional hydrazino or oxyamino modification reagents provided herein to incorporate a hydrazino or oxyamino function respectively.

In yet another embodiment, oligonucleotides prepared via polymerases or reverse transcriptases with nucleoside triphosphates possessing an amino group can be post-synthetically modified to incorporate a hydrazino or oxyamino group using the bifunctional hydrazino or oxyamino reagents provided herein. The modified oligonucleotides can be subsequently covalently linked to reporter molecules possessing carbonyl groups.

C. Hydrazone Conjugates Prepared from Aliphatic Hydrazines and Aliphatic Carbonyls for in Vivo Uses Provided herein are hydrazone conjugates prepared form aliphatic hydrazines and aliphatic carbonyls for in vivo uses, e.g., as vaccines. Use of bacterial polysaccharides as vaccines does not lead to an efficient immune response. It has been demonstrated that conjugation of the polysaccharide to a protein such as tetanus toxoid or diptheria toxoid leads to an effective immune response (R. W. Ellis and D. M. Granoff, Development of Clinical Uses of Haemophilus b Conjugate Vaccines, Marcel Dekker, Inc., New York (1994)). This has been demonstrated by the success of protein/polysaccharide vaccines described therein.

A common property of all these conjugate vaccines is that the nature of the covalent linkage is aliphatic. The use of aromatic groups in the covalent linkage leads to immune responses to the aromatic epitope. This results in reduced immune response.

Thus, in one embodiment, the hydrazino and oxyamino bifunctional reagents provided herein can be used to modify protein carriers such as tetanus toxoid or diptheria toxoid in a single step. These hydrazino or oxyamino modified carriers are reacted with bacterial polysaccharides that have been oxidized with sodium periodate to form dialdehyde moieties. The use of hydrazino and oxyamino moieties are preferred to conjugates mediated by amino or hydrazide moieties as no reducing reagent is required to form a stable linkage.

D. Hydrazino and Oxyamino Modified Beads

In another embodiment, hydrazino and oxyamino modified beads are provided. The hydrazino and oxyamino modified beads are prepared by reaction of an appropriate bead, e.g., one that possesses an amino or a thiol group, with a bifunctional reagents provided herein.

Modified latex and silica beads have found wide utility in diagnostic assays (www.bangslabs.com, Bangs Laboratories, Terre Haute, Ind.). A variety of modified beads are available including amino, thiol and hydrazide beads to link for the purpose of covalent linkage of biomolecules. Provide herein are hydrazino and oxyamino beads prepared using bifunctional hydrazino and oxyamino reagents provided herein to convert amino modified beads to hydrazino or oxyamino modified beads. Hydrazino modified beads will form stable hydrazones when reacted with molecules possessing carbonyl groups.

This is preferable to methods linking acid modified beads to molecules possessing amino groups for two reasons. First no activation of the bead is required. The method used to activate acid beads requires treatment of the bead with N-hydroxysuccinimide/ethyldimethylethyl-aminocarbodiimide (EDCI) followed by washing and addition of the amine. The activated bead has limited stability in water and the amino function on the molecule to be immobilized is poorly nucleophilic at the pHs used for linking (pH 4.7–9.0). Both the carbonyl and hydrazino or oxyamino couple described herein have infinite stability in water and the hydrazone forms without mediation by a condensing or reducing reagent.

E. Silane Hydrazines for Modification of Silica Surfaces

In further embodiments, hydrazino and oxyamino silanes are provided. These reagents are useful for modification of silica surfaces to generate hydrazino and oxyamino glass, including, but not limited to, controlled pore glass; hydrazino and oxyamino slides; and hydrazino and oxyamino silica chips.

The development of both DNA-based and protein microarrays has led to a revolution in biotechnology. These microarrays are based on immobilization of tens to tens of thousand biomolecules on solid surfaces. Silica based surfaces such as glass slides and silica chips have been the surface of choice to prepare microarrays. The immobilization of biomolecules requires attachment of the biomolecules via covalent or non-covalent, i.e., electrostatic, interactions. Glass slides modified to incorporate amino or aldehyde groups are commercially available (www.arrayit.com, Telechem, Inc. Sunnyvale, Calif. and www.cel-1.com, Cel Associates, Houston, Tex.). Protocols to immobilize oligonucleotides or polynucleotides require the use of strong chemical conditions such as sodium borohydride or crosslinking conditions such as photolysis. These methods are inefficient and cause direct modification of the oligonucleotide leading to reduced affinity towards its complementary target.

Thus, provided herein are hydrazine-based silane reagents for preparation of hydrazine-modified silica based surfaces that overcome these deficiencies. In one embodiment, the reagent is a bifunctional silane hydrazine of formulae XI:

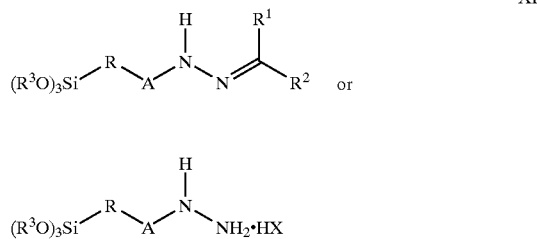

XI or a derivative thereof, where $R^3$ is a straight chain, branched or cyclic alkyl group of 1–10 carbons; $R^1$ is H or a saturated straight chain of 3 to 20 carbon atoms, a chain of 2 to 2000 ethyleneoxide moieties, or a saturated or unsaturated carbocyclic moiety of 3 to 20 carbon atoms; $R^2$ is a saturated straight chain of 3 to 20 carbon atoms, a chain of 2 to 2000 ethyleneoxide moieties, or a saturated or unsaturated carbocyclic moiety of 3 to 20 carbon atoms; X is a negative counterion, including halide, pseudohalide, sulfate, phosphate, boronate, an organic carboxylate, including, but not limited to, trifluoroacetate, and the anion of an inorganic acid; R is an aliphatic divalent group having any combination of the following groups, which are combined in any order: cycloalkylene, $C(R^{10})_2$, —$C(R^{10})$=$C(R^{10})$—, >C=$C(R^{12})(R^{13})$ >$C(R^{12})(R^{13})$, —C≡C—, O, $S(G)_a$, $P(J)_b(R^{10})$, $P(J)_b(LR^{10})$, $N(R^{10})$, >$N^+(R^{12})(R^{13})$ and C(L); where the variables are as defined above; and A is a direct link, NH(C=O), NH(C=S), NHNH(C=O), or NHNH(C=S). In certain embodiments, R is a straight chain, branched or cyclic alkyl group of 2–15 carbons, a polyethyleneglycol moiety of 2–2000 monomers or an aromatic group, or can incorporate a cleavable moiety such as a disulfide.

In one embodiment, the reagents have the formula:

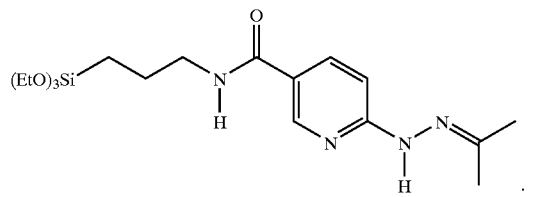

In other embodiments, the silane modification reagents are oxyamino compounds of formula XII:

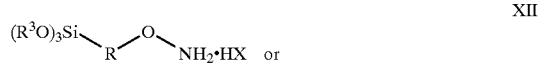

XII

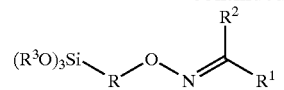

or a derivative thereof, where $R^3$ is a straight chain, branched or cyclic alkyl group of 1–10 carbons; $R^1$ is H or a saturated straight chain of 3 to 20 carbon atoms, a chain of 2 to 2000 ethyleneoxide moieties, or a saturated or unsaturated carbocyclic moiety of 3 to 20 carbon atoms; $R^2$ is a saturated straight chain of 3 to 20 carbon atoms, a chain of 2 to 2000 ethyleneoxide moieties, or a saturated or unsaturated carbocyclic moiety of 3 to 20 carbon atoms; X is a negative counterion, including halide, pseudohalide, sulfate, phosphate, boronate, an organic carboxylate, including, but not limited to, trifluoroacetate, and the anion of an inorganic acid; and R an aliphatic divalent group having any combination of the following groups, which are combined in any order: cycloalkylene, $C(R^{10})_2$, —$C(R^{10})$=$C(R^{10})$—, >C=$C(R^{12})(R^{13})$, >$C(R^{12})(R^{13})$, —C≡C—, O, $S(G)_a$, $P(J)_b(R^{10})$, $P(J)_b(LR^{10})$, $N(R^{10})$, >$N^+(R^{12})(R^{13})$ and C(L); where the variables are as defined above. In certain embodiments, R is a straight chain, branched or cyclic alkyl group of 2–15 carbons, a polyethyleneglycol moiety of 2–2000 monomers or an aromatic group, or can incorporate a cleavable moiety such as a disulfide.

F. Metals/Particles

Figure 8:
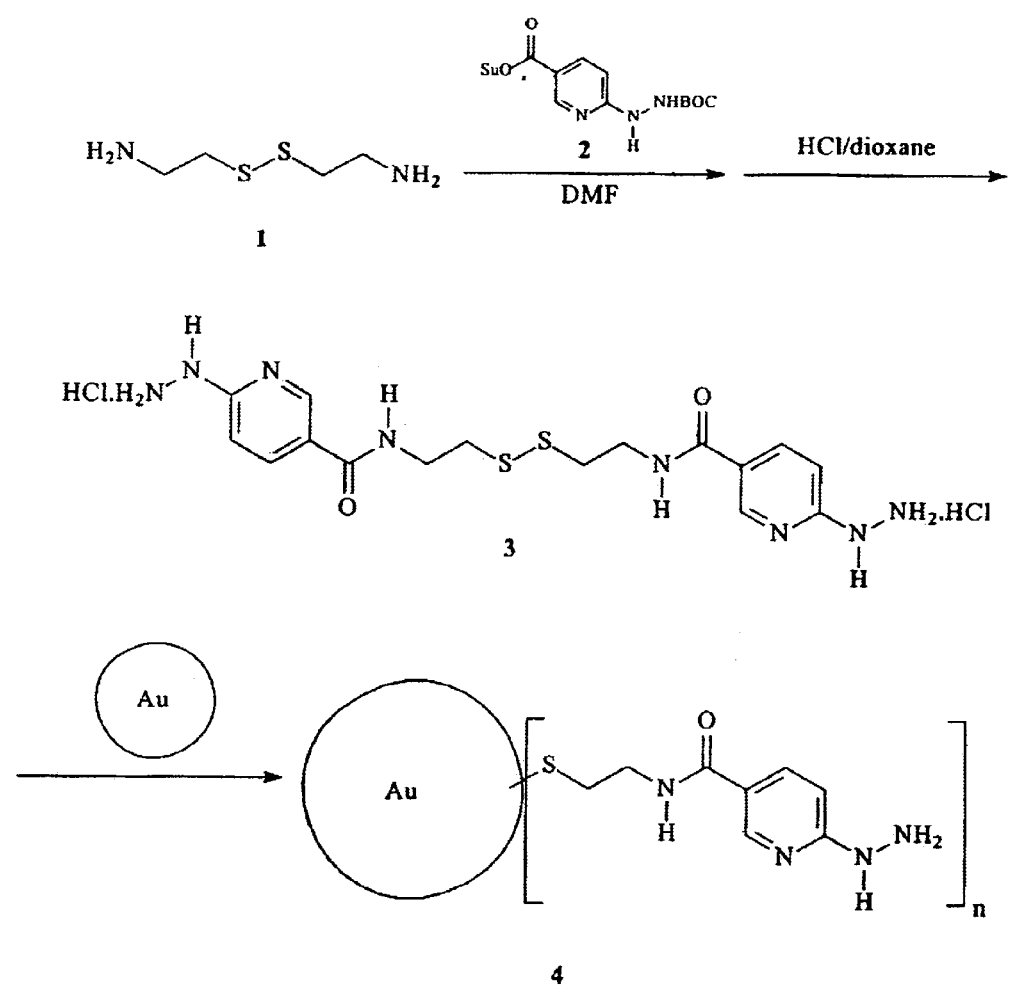
FIG. 8 is a synthetic scheme for the preparation of a bishydrazinium hydrochoride disulfide and its covalent linkage to gold particles.

In another embodiment, reagents to incorporate hydrazino and oxyamino groups on thiophilic metals, surfaces and particles are provided. Thiol hydrazine, disulfidedihydrazine, thioloxyamino and disulfidedioxyamino reagents will react directly with gold particles to form an Au-S bond thereby incorporating a hydrazine or oxyamino group on the gold particle (see, e.g., FIG. 8). The hydrazine or oxyamino group can subsequently be linked to any molecule possessing a carbonyl function. In a further embodiment, the carbonyl possessing molecules include biomolecules, including, but not limited to, proteins, peptides, polynucleotides, synthetic oligonucleotides and carbohydrates. The carbonyl group can be incorporated on the biomolecule using amino reactive carbonyl bifunctional reagents such as succinimidyl 4-formylbenzoate (SFB) or by periodate-mediated oxidation of endogenous carbohydrates to produce dialdehydes.

In one embodiment, the reagents for use in the methods provided herein have formulae XIII:

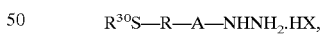

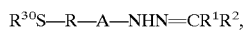

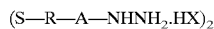

or

or a derivative thereof, wherein R, $R^1$, $R^2$ and X are as defined above; A is A is a direct link, C=O, C=S, NH(C=O), NH(C=S), NHNH(C=O), or NHNH(C=S); and $R^{30}$ is hydrogen or a thiol protecting group, including, but not limited to, a substituted or unsubstituted benzyl group, a thioester including S-acetyl and S-benzoyl thioesters, a thiocarbonate, a thiocarbamate, or $SR^{31}$; where $R^{31}$ is alkyl, aryl, aralkyl, heteroaryl or heteroaralkyl.

In this embodiment, the reagents include:

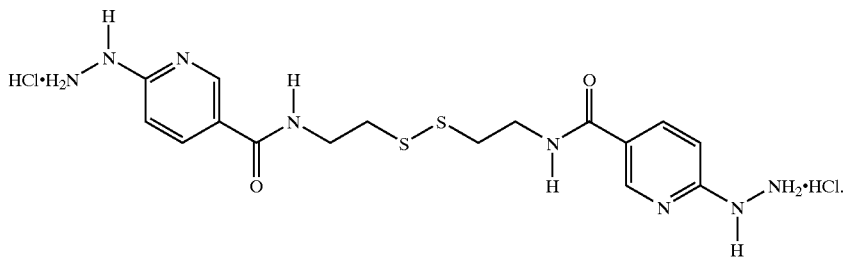

In another embodiment, the reagents for use in the methods provided herein have formulae XIII:

$R^{30}S-R-ONH_2 \cdot HX$, $R^{30}S-R-ON=CR^1R^2$, $(S-R-ONH_2 \cdot HX)_2$ or $(S-R-ON=CR^1R^2)_2$;

or a derivative thereof, wherein R, $R^1$, $R^2$ and X are as defined above; and $R^{30}$ is hydrogen or a thiol protecting group, including, but not limited to, a substituted or unsubstituted benzyl group, a thioester including S-acetyl and S-benzoyl thioesters, a thiocarbonate, a thiocarbamate, or $SR^{31}$; where $R^{31}$ is alkyl, aryl, aralkyl, heteroaryl or heteroaralkyl.

G. Preparation of the Reagents

The preparation of an aliphatic or aromatic bifunctional semicarbazide or thiosemicarbazide may be accomplished by treatment of a phosgene or thiophosgene substituted amine, respectively, in the presence of base.

In one embodiment, the reagents of formula I are prepared by initially preparing the hydrazine-based acid and subsequently protecting the hydrazine-moiety with a acid sensitive protecting group including, but not limited to, a tert-butoxycarbonyl (BOC) group. Subsequently the acid moiety is converted into a N-hydroxysuccinimidyl ester. The BOC-protected hydrazine succinimidyl ester is deprotected using anhydrous acid in an organic solvent such as hydrogen chloride/dioxane. The treatment removes the BOC group while simultaneously protecting the hydrazine as its hydrochloride salt. The succinimidyl ester/hydrochloride salt product precipitates and is isolated.

In another embodiment, the amino group of a molecule containing a BOC-protected hydrazine moiety is converted into a maleimido moiety. The maleimido/BOC-protected molecule is treated with an anhydrous acid such as trifluoroacetic acid in dichloromethane to remove the BOC group and protect the hydrazine as its trifluoroacetate salt. The product is isolated by removal of solvent.

Bifunctional carbazides or thiocarbazides may be prepared by treatment of a hydrazine with phosgene or thiophosgene, respectively, in the presence of base followed by isolation of the iso(thio)cyanate. Addition of hydrazine yields the desired carbazide or thiocarbazide respectively.

Bifunctional semicarbazides or thiosemicarbazides may be prepared by treatment of an amine with phosgene or thiophosgene, respectively, in the presence of base followed by isolation of the iso(thio)cyanate. Addition of hydrazine yields the desired semicarbazide or thiosemicarbazide respectively.

Other reagents provided herein are hydrazones, which are prepared from bifunctional hydrazine intermediates as described for compounds of formula I above by treatment of these compounds with an aliphatic aldehyde or ketone to protect the hydrazine as its hydrazone. The alkyl group on the aliphatic aldehydes is chosen form straight chain of 1–20 carbon atoms, cyclic or polycyclic aliphatic rings of 3–10 carbons or branched chains of 3–20 atoms or any combination of the aliphatic moieties. The alkyl groups on a dialiphatic ketone are chosen from similar aliphatic groups described for the substitution on the aliphatic aldehyde.

Bifunctional hydrazides may be prepared by condensation of a bifunctional molecule possessing an acid moiety with a mono-protected carbazate in the presence of a dehydrating reagent (e.g, dicyclohexylcarbodiimide) followed by deprotection.

H. Methods of Use

Figure 2:
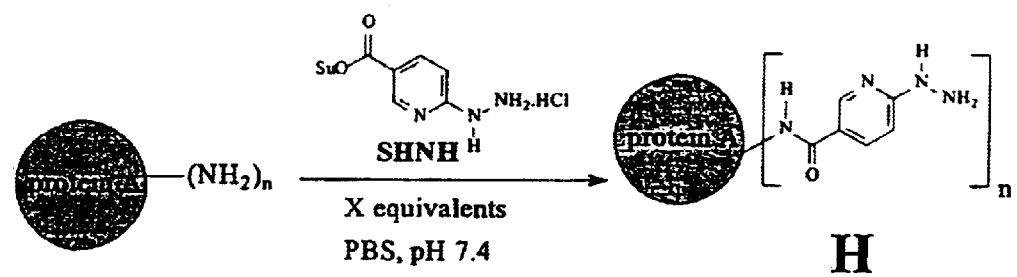
FIG. 2 illustrates a scheme for hydrazine and aldehyde incorporation on biomolecules and the conjugation of the two modified biomolecules.
Figure 2:
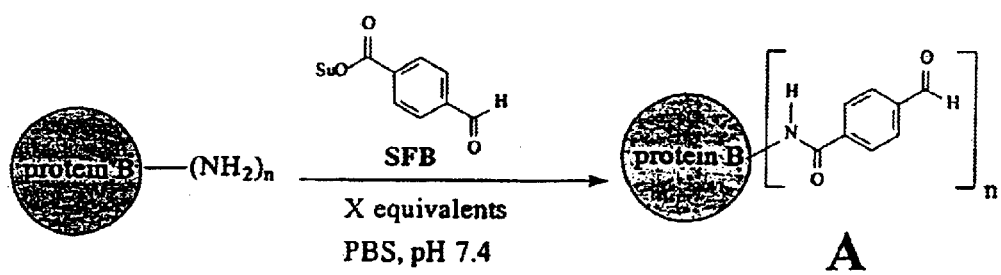
Figure 2:
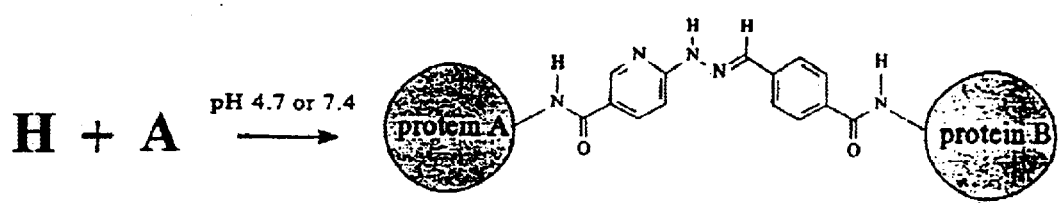

Also provided herein are methods of preparation of conjugates formed by the reaction of the hydrazine-modified molecules with the carbonyl-containing or carbonyl-modified molecules, hydrazine-modified molecules with carbonyl-modified surfaces or carbonyl-containing or carbonyl-modified molecules with hydrazine-modified surfaces. Conjugates are also provided. When the modified molecules provided herein are reacted a stable covalent hydrazone or oxime bond is formed crosslinking the two modified molecules (see, e.g., FIG. 2) or the modified molecules to a modified surface.

Hydrazino-containing conjugates may be generally prepared by addition of a solution of a bifunctional hydrazino modification reagent provided herein to a biomolecule or water-soluble synthetic molecule in a non-nucleophilic buffer at pH 7.0–8.0. Modification of an organic soluble natural or synthetic molecule such as a hydrophobic peptide can be performed in organic solution by direct addition of the protected bifunctional hydrazino molecule to an organic soluble compound possessing an amine or thiol substituted moiety.

The reagent provided herein may be utilized to form crosslinks between a wide variety of molecules, including for example protein—protein conjugates (e.g., monoclonal antibody/enzyme conjugate) or protein-polymer conjugates (e.g., monoclonal antibody to a microtiter well surface). Many polymers and solid surfaces containing aldehyde moieties are commercially available and are generally utilized to crosslink amine containing molecules. This method binds a desired protein or an oligonucleotide containing a terminal amine by in situ formation of an imine bond followed by reduction of the imine with sodium cyanoborohydride to form a stable alkylhydrazide bond. Modification of molecules to possess hydrazines for binding to surfaces allows direct stable covalent attachment of the molecule to these carbonyl-containing supports with higher efficiency than current methods because the crosslinking couples of the present invention have far superior aqueous stability than currently known crosslinking couples.

Conjugated biomolecules may be crosslinked by incubation at ambient temperature of a hydrazine-modified biomolecule and a carbonyl-modified biomolecule. The crosslinked product may be isolated by gel permeation chromatography.

Immobilization of biomolecules to surfaces using this crosslinking couple is accomplished by modifying the biomolecule with either a hydrazino, oxyamino or a carbonyl moiety and contacting the modified biomolecule to a surface possessing its reactive partner, e.g., a hydrazino or oxyamino moiety for a carbonyl-modified biomolecule, or a carbonyl moiety for a hydrazino- or oxyamino-modified biomolecule.

In one embodiment, the carbohydrate domain of an antibody that is not involved in antigen binding is oxidized with sodium periodate to yield aldehyde moieties. These aldehyde moieties react directly with hydrazino- or oxyamino-modified surfaces to yield a stable covalent linkage in which a large percentage of the antibody active sites are available for antigen binding. Due to the increased efficiency of this method, a significantly lower amount of monoclonal antibody is required for conjugation to the surface and correspondingly increase the sensitivity of the assays. Current ELISA protocols use non-specific binding of antibodies to plastic surfaces that results in <5% of antigen binding sites available for antigen capture.

As provided herien, the reaction of a hydrazino moiety with a carbonyl moiety forms a hydrazone linkage. The reaction of an oxyamino moiety with a carbonyl moiety forms an oxime. Kaneko et al. (1991) *Bioconjugate Chem.* 2:133 have demonstrated that hydrazones formed from the reaction of an aryl hydrazine and an aromatic ketone (adriamycin) is stable at the pH range 4.7–7.4. It is known that bisarylhydrazones formed from an aromatic hydrazine and an aromatic carbonyl are more stable than hydrazones formed from aliphatic hydrazines and aliphatic carbonyls as the delocalization of electrons in the aromatic system increases the stability of the hydrazone to nucleophilic attack by nucleophiles such as water. Therefore, in one embodiment, hydrazones formed from the reaction of an aromatic hydrazine and an aromatic carbonyl are employed for in vitro uses.

The following examples are included for illustrative purposes only and are not intended to limit the scope of the invention.

EXAMPLE 1

Preparation of a Succinimidyl Carbocyclic Thiosemicarbazide Hydrochloride

Figure 3:
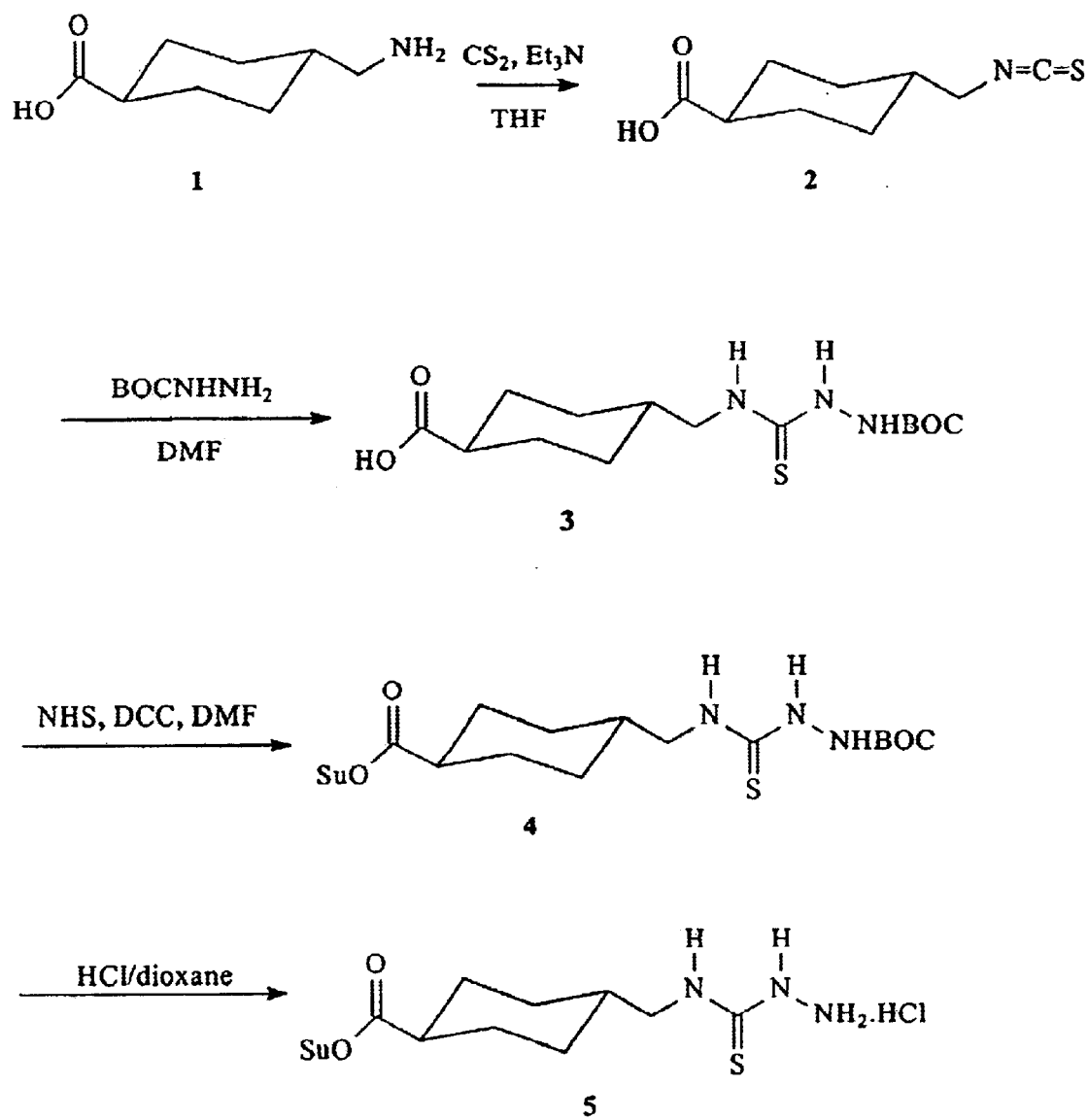
FIG. 3 is a synthetic scheme for the preparation of a bifunctional amino reactive aliphatic thiosemicarbazide hydrochloride.
Figure 4:
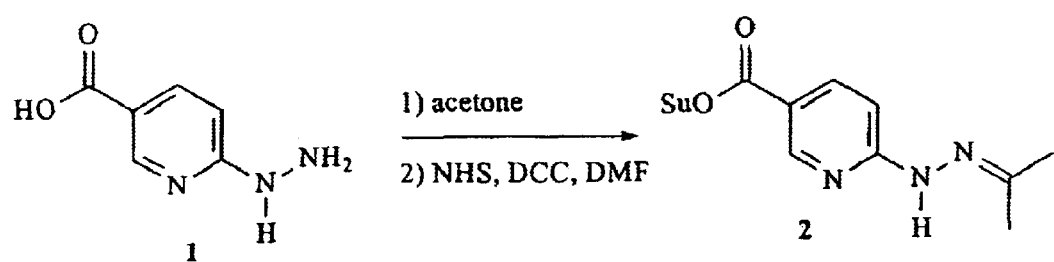
FIG. 4 is a synthetic scheme for the preparation of succinimidyl 6-hydrazinonicotinate acetone hydrazone (SANH).

As shown in FIG. 3, to a suspension of 4-aminomethylcyclohexane carboxylic acid (1.0 equivalent; Aldrich Chemical, Milwaukee, Wis.) and triethylamine (2.1 equivalents) in THF is added thiophosgene (1.0 equivalent). The reaction mixture is stirred at room temperature until homogeneous. The solvent is removed under reduced pressure and the residue is used without further purification.

To a solution of this residue in DMF is added t-butyl carbazate (1.0 equivalent; Aldrich Chemical Company, Milwaukee, Wis.) in DMF. The reaction mixture is stirred at room temperature for 2 hours. The solvent is removed under reduced pressure and the residue is partitioned between ethyl acetate and 5% aqueous citric acid. The organic phase is washed with brine, dried over magnesium sulfate, filtered and concentrated to give 4-(tert-butoxycarbonylthiosemicarbazidomethyl)cyclohexane carboxylic acid.

This compound (1.0 equivalent) is dissolved in DMF and N-hydroxysuccinimide (1.0 equivalent) is added followed by the dropwise addition of a solution of dicyclohexylcarbodiimide (1.0 equivalents) in DMF. The reaction mixture is stirred at room temperature for 4 hours. The dicyclohexylurea (DCU) precipitate byproduct is removed by filtration and the filtrate is concentrated to dryness. The residue is partitioned between ethyl acetate and 5% aqueous citric acid. The organic phase is washed with brine, dried over magnesium sulfate, filtered and concentrated to give succinimidyl 4-(tert-butoxycarbonylthiosemicarbazidomethyl) cyclohexane carboxylate.

The resulting compound is dissolved in dry dioxane and an equivalent volume of 4 M HCl/dioxane (Aldrich Chemical Company, Milwaukee, Wis.) is added and the reaction mixture is allowed to stir at room temperature overnight. The precipitated product is isolated by initially bubbling argon through the reaction mixture to remove excess HCl. The suspension is centrifuged and the supernatant discarded. The pellet is treated with dry dioxane resuspended, recentrifuged and the supernatant discarded. The washing is repeated two additional times. The solids are dried in a vacuum oven to give succinimidyl 4-(thiosemicarbazidomethyl)cyclohexane carboxylate hydrochloride.

EXAMPLE 2

Preparation of Succinimidyl 6-Hydrazinonicotinate Acetone Hydrazone

Hydrazinonicotinic acid (1 mmol; U.S. Pat. No. 5,206, 370) was suspended in acetone and the suspension stirred at room temperature for 1 hour. The solids were isolated by filtration to give the desired hydrazone.

This hydrazone (1.0 equivalent) was suspended in DMF end N-hydroxysuccinimide (NHS)(1.0 equivalent) was added and followed by the addition of a solution of DCC (1.0 equivalent) in DMF. The reaction mixture was stirred at room temperature for 16 hours. The heterogeneous reaction mixture was filtered and the filtrate was concentrated under reduced pressure. The residue was dissolved in a minimum amount of ethyl acetate and hexanes were added to turbidity. A pale yellow precipitate formed that was isolated by filtration to give the desired compound with an approximate yield of 33%. PMR (DMSO-$d_6$) δ 1.99 (s, 3H), 2.00 (s,3H), 3.32 (s, 4H), 7.17 (D, 1H), 8.12 (dd, 1H), 8.76 (d, 1H), 10.39 (s, 1H).

EXAMPLE 3

Preparation of a Maleimide Carbocyclic Hydrazide Trifluoroacetate

To a suspension of 4-aminomethylcyclohexane carboxylic acid (1 mmol) in DMF is added triethylamine (1.1 mmol) and t-butylcarbazate (1 mmol, Aldrich Chemical Co., Milwaukee, Wis.) followed by the dropwise addition of DCC (1.0 mmol) in DMF. The reaction mixture is stirred at room temperature for 4 hours. The solvent is removed under reduced pressure and the residue is treated with ethyl acetate and the solids (DCU) are removed by filtration. The filtrate is concentrated and the residue is chromatographed on silica gel using ethyl acetate as eluant. The fractions containing product are pooled and concentrated.

To a solution of the resulting compound (1 mmol) in THF is added maleic anhydride (1 mmol), the reaction mixture is stirred at room temperature and acetic anhydride (1 mmol)

and triethylamine (1 mmol) are added. Following stirring at room temperature for 16 hours, the solvent is removed under reduced pressures and the residue is chromatographed on silica gel using ethyl acetate as eluant. The fractions containing product are pooled and concentrated.

A solution of this compound in methylene chloride is treated with a solution of trifluoroacetic acid/methylene chloride (1/1) and stirred at room temperature for 2 hours. The volatiles are removed under reduced pressure and the product is subsequently co-evaporated with MeOH/toluene to remove the excess trifluoroacetic acid.

EXAMPLE 4

Preparation of Carbocyclic Succinimidyl Thiosemicarbazide Hydrochloride

To a suspension of proline (1 mmol) in THF is added triethylamine (2.5 mmol) followed by the dropwise addition of a solution of thiophosgene (1.1 mmol). The reaction mixture is stirred at ambient temperature for 4 hours followed by cooling the reaction mixture to 0° C. and the dropwise addition of a solution of t-butyl carbazate (1.1 mL). The reaction mixture is stirred at 0° C. for 1 hour and at room temperature for 2 hours. The solvent is removed under reduced pressure, and the residue is chromatographed on silica gel using methylene chloride/methanol (9/1) as eluant. The fractions containing product are pooled and concentrated.

To a solution of this compound (1 mmol) in THF is added N-hydroxysuccinimide (1 mmol) followed by the dropwise addition of DCC (1.0 mmol) in THF. The reaction mixture is stirred at room temperature for 3 hours and the DCU precipitate is removed by filtration. The filtrate is concentrated under reduced pressure and the residue is chromatographed on silica gel using ethyl acetate as eluant. The fractions containing product are pooled and concentrated.

To a solution of this compound in dioxane is added 4 M hydrochloride/dioxane (Aldrich Chemical Co., Milwaukee, Wis.). The reaction mixture is stirred at room temperature for 16 hours during which time a precipitate formed. Argon is bubbled through the reaction mixture to remove excess hydrogen chloride. The heterogeneous reaction mixture is centrifuged and the supernatant is discarded. The pellet is treated with dry dioxane, vortexed and recentrifuged. The dioxane wash is repeated two additional times. The product is dried in a vacuum oven.

EXAMPLE 5

Preparation of a Succinimidyl Semicarbazido-PEG-Hydrazone

Figure 6:
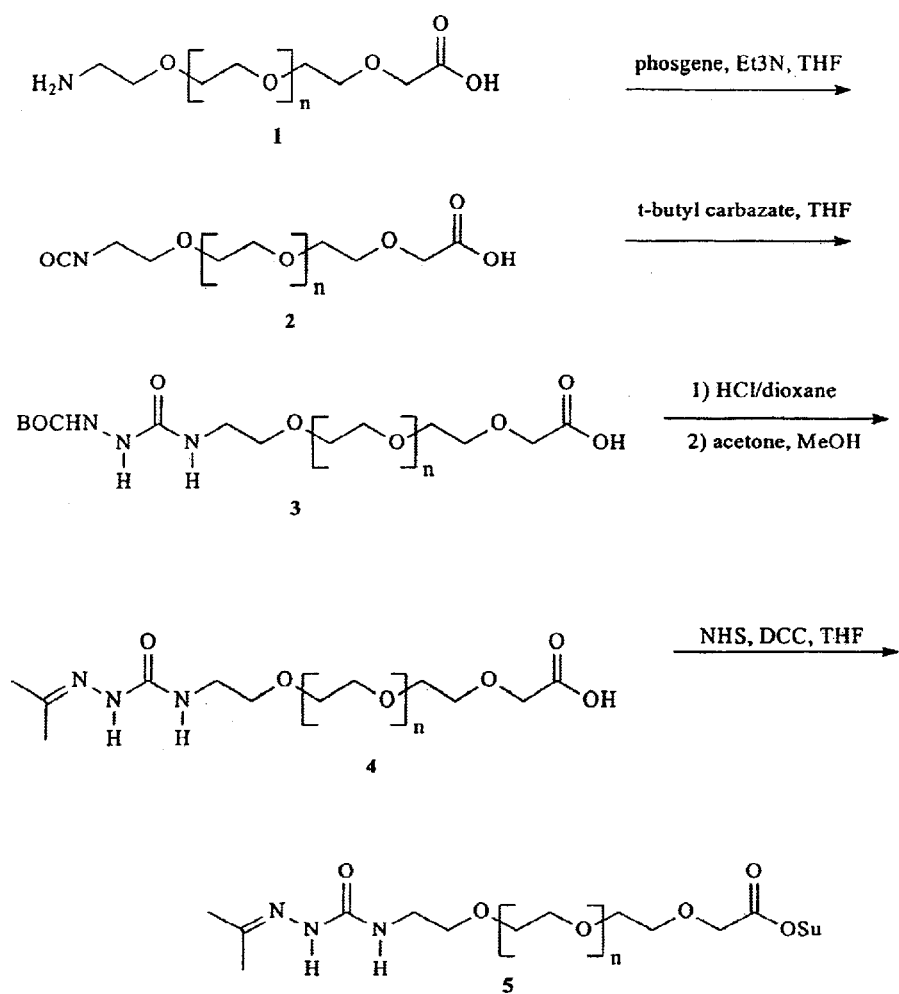
FIG. 6 is a synthetic scheme for the preparation of bifunctional hydrazone protected carbazido-PEG-succinimidyl ester.
Figure 7:
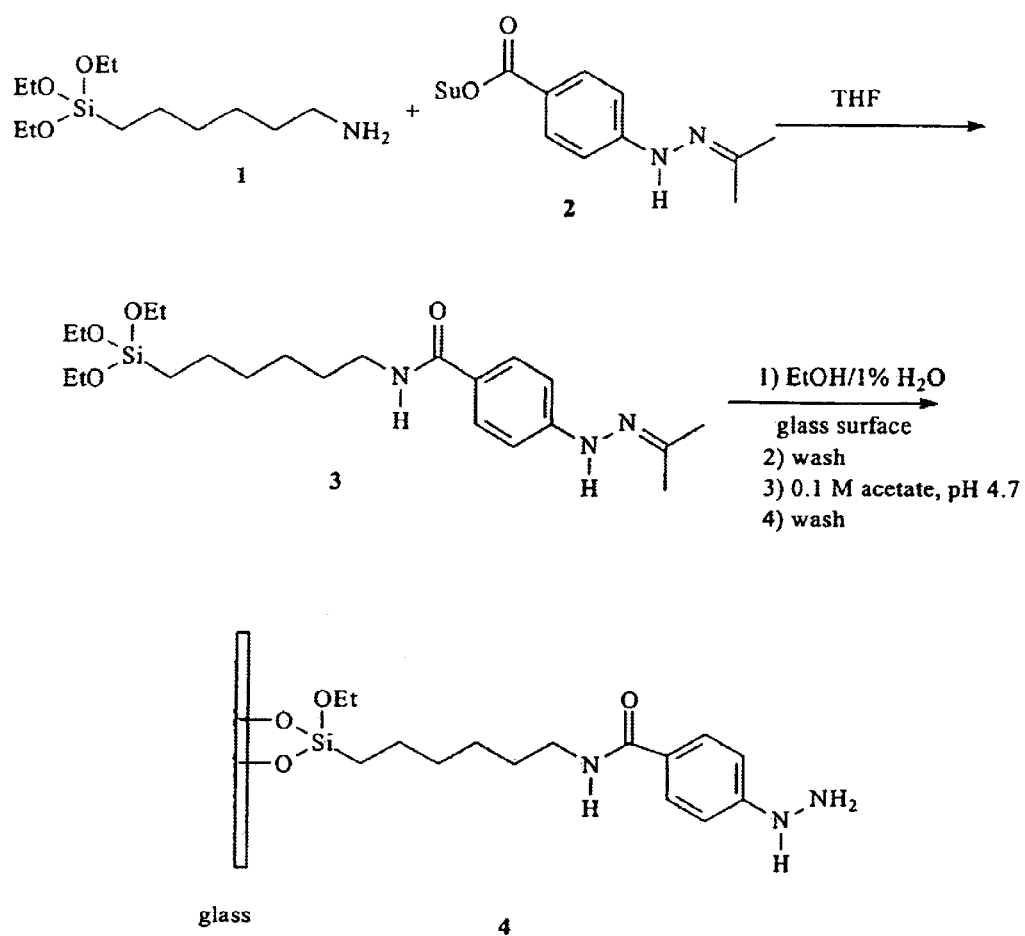
FIG. 7 is a scheme for the preparation of silane hydrazone-protected hydrazine and its subsequent immobilization on a silica based surface.

As shown in FIG. 6, to a solution of aminoethyl-PEG-acetic acid (see, FIG. 6, compound 1, 1 mmol; Shearwater Polymers, Birmingham, Ala.) in THF is added triethylamine (2.2 mol) and phosgene (1 mmol). The reaction mixture is stirred at room temperature for 2 hours and the solvent is removed and the product isolated by silica gel chromatography.

To a solution of this compound (1 mmol) in THF is added a solution of t-butyl carbazate (1 mmol). The reaction mixture is stirred at room temperature for 2 hours. The solvent is removed under reduced pressure and the resulting BOC-protected semicarbazide is isolated by silica gel chromatography.

To a solution of this compound in dioxane is added 4 M HCl/dioxane and the reaction mixture is stirred at room temperature for 2 hours. Argon is bubbled through the reaction mixture to remove excess HCl followed by removal of the solvent under reduced pressure. The residue is co-evaporated from dioxane twice. The residue is resuspended in methanol and treated with acetone (1.1 mmol) and stirred at room temperature for 1 hour. The reaction mixture is concentrated under reduced pressure and the residue containing the desired hydrazone acid is dissolved in THF. The solution is treated with NHS (1 mmol) followed by the dropwise addition of DCC (1 mmol) in THF. Following stirring at room temperature for 3 hours, the DCU precipitate is removed by filtration and the product is isolated by silica gel chromatography.

EXAMPLE 6

Preparation of a Hydazone-Protected Hydrazine Silane Reagent and Modification of Glass Surfaces a. Hydrazone-Protected Hydrazine Silane Reagent To a solution of triethoxyaminopropylsilane (United Chemical Technologies, Bristol, Pa.; 1.0 equivalent) in THF was added a solution of succinimidyl 4-hydrazinonicotinate acetone hydrazone (1.0 equivalent). The reaction mixture was stirred at room temperature for 4 hours. A precipitate formed on the sides of the flask. The reaction mixture was filtered thru a plug of cotton wool and the filtrate was concentrated to dryness under reduced pressure. The residue contained an equimolar mixture of desired silane hydrazone and N-hydroxysuccinimide. The mixture was used directly to modify glass surfaces.

b. Modification of Glass Surfaces

Glass microscope slides are prepared by immersion in 0.1 M NaOH solution for 1 hour. The slides are subsequently washed with water and ethanol and dried in a vacuum oven. The slides are immersed in 5% solution of the compound of EXAMPLE 6.a. in 98% ethanol/2% water and incubated at room temperature for 4 hours. The slides are washed with ethanol, water and ethanol again. The slides are dried in a vacuum oven overnight.

EXAMPLE 7

Preparation of 96 Well Plates to Incorporate Aromatic Aldehyde Moieties

Amino-modified 96 well plates (Costar or Corning) are modified with succinimidyl 4-formylbenzoate (SFB) as follows. A fresh solution of SFB (1.25 mL of 10 mg/mL) in DMSO is prepared. This solution is diluted into phosphate buffered saline (PBS)(0.1 M phosphate, 0.15 M NaCl, pH 7.4: 100 mL). To each well is added 200 µL of the SFB/PBS solution and the wells are incubated at room temperature for 4 hours. The wells are washed three times with PBS/0.5% Tween®. The wells are dried and are ready for protein conjugation.

EXAMPLE 8

Preparation of 96 Well Plates to Incorporate Aromatic Hydrazine Moieties

Amino-modified 96 well plates (Costar or Corning) are modified with succinimidyl acetone nicotinic acid hydrazone (SANH) as follows. A fresh solution of SANH (1.25 mL of 10 mg/mL) in DMSO is prepared. This solution is diluted into PBS (0.1 M phospate, 0.15 M NaCl, pH 7.4: 100 mL). To each well was added 200 j µL of the SIFBIANH/PBS solutions and the wells were incubated at room temperature for 4 hours. The wells are washed with water and then treated with 0.1 M acetate, pH 4.7 (200 μL) for 2 hours. The wells were washed three times with PBS/0.5% Tween. The wells were dried and are ready for conjugation to molecules possessing carbonyl moieties.

EXAMPLE 9

General Procedure for the Modification of a Protein with a Succinimidyl Carbazidyl Modification Reagent A 5 mg/mL solution of bovine serum albumin in PBS (100 mM phosphate. 150 mM NaCl, pH 7.4 and 2 mM EDTA) (200 μL; 1 mg protein) is prepared. A solution of succinimidyl 4-semicarbazidylbenzoate hydrochloride (SSCH; 3.5 mg) in DMF (100 μL) is prepared. To the protein solution is added the SSCH/DMF solution (30 equivalents). The reaction mixture is incubated at room temperature for 4 hours. The modified protein is isolated by placing the reaction mixture in a 30K ultra-free centrifugation device and washing three times with conjugation buffer (3×400 μL). The purified protein is quantitated for protein concentration (BCA assay) and for hydrazine modification level by addition of 0.2 mM 2-p-nitrobenzaldehyde in PBS pH 7.4 and measuring the absorbance at 380 nm (extinction coefficient 22,600).

EXAMPLE 10

General Procedure for the Modification of a Protein with a Succinimidyl Carbonyl Modification Reagent A 5 mg/mL solution of polyclonal IgG in PBS (100 mM phosphate, 150 mM NaCl, pH 7.4) and 2 mM EDTA (200 μL; 1 mg protein) was prepared. A solution of succinimidyl 4-formylbenzoate (SFB; (2 mg) in DMF (50 μL) is prepared. To the protein solution was added the SFB/DMF solution (15 eq.). The reaction mixture was incubated at room temperature for 4 hrs. The modified IgG was isolated and buffer exchanged by placing the reaction mixture in a 30K ultra-free centrifugation device and washing three times with 0.1 M MES, 0.9% NaCl, pH 4.7 (3×400 μL). The purified protein was quantified for protein concentration (BCA assay; Pierce Chemical Co., Rockford, Ill.) and for carbonyl modification level by incubation of an aliquot of protein in a 0.2 mM 2-hydrazinopyridine in 0.1 M MES, 0.9% NaCl, pH 4.7 and measuring the absorbance at 360 nm (molar extinction coefficient 20,000).

EXAMPLE 11

General Procedure for Preparation of a Hydrazine-Modified Protein

A 5 mg/mL solution of ovalbumin in PBS (100 mM phosphate, 150 mM NaCl, pH 7.4) and 2 mM EDTA (200 μL; 1 mg protein) was prepared. A solution of succinimidyl 6-hydrazinonicotinate acetone hydrazone (SANH) (EXAMPLE 2)(2 mg) in DMF (50 μL) is prepared, To the protein solution was added the SANH/DMF solution (15 eq.). The reaction mixture was incubated at room temperature for 4 hours. The modified protein was isolated and buffer exchanged by placing the reaction mixture in a 30K ultra-free centrifugation device and washing three times with 0.1 M MES. 0.9% NaCl, pH 4.7 (3×400 μL). The purified protein was quantified for protein concentration (BCA assay; Pierce Chemical Co., Rockford, Ill.) and for hydrazine modification level by incubation of an aliquot of protein in a 0.5 mM 4-nitrobenzaldehyde in 0.1 M MES, 0.9% NaCl, pH 4.7 and measuring the absorbance at 360 nm (molar extinction coefficient 22,000).

EXAMPLE 12

General Procedure for the Preparation of a Conjugate by Reaction of a Hydrazine Modified Protein with a Carbonyl Modified Protein Aldehyde-modified IgG (EXAMPLE 10) in MES (1 mg; 0.200 μL of a 2.5 mg/mL solution) was added to a solution of hydrazine-modified ovalbumin (EXAMPLE 11, 1 mL; 0.200 μL of a 5 mg/mL solution), and the reaction mixture was incubated at room temperature for 4 hours. The reaction mixture was analyzed by PAGE gel (coomassie blue development) that demonstrated presence of a high molecular weight product and 5% unreacted aldehyde-modified IgG and <10% unreacted hydrazine-modified ovalbumin. The level of conjugation is quantified by measuring the absorbance at 360 nm.

EXAMPLE 13

Preparation of a Thiosemicarbazide Modified Protein

A 5 mg/mL solution of ovalbumin in PBS (100 mM phosphate, 150 mM NaCl, pH 7.4) and 2 mM EDTA (200 μL; 1 mg protein) was prepared. A solution of succinimidyl 4-thiosemicarbazidylbenzoate hydrochloride (STBH) (2 mg) in DMF (50 μL) is prepared. To the protein solution was added the STBH/DMF solution (15 eq.). The reaction mixture was incubated at room temperature for 4 hours. The modified protein was isolated and buffer exchanged by placing the reaction mixture in a 30 K ultra-free centrifugation device and washing three times with 0.1 M MES, 0.9% NaCl. pH 4.7 (3×400 μL). The purified protein was quantified for protein concentration (BCA assay; Pierce Chemical Co., Rockford, Ill.).

EXAMPLE 14

Conjugation of a Thiosemicarbazide-Modified Protein to an Aldehyde Modified Protein The thiosemicarbazide protein prepared in EXAMPLE 13 was reacted with aldehyde-modified protein in an identical manner as described for the hydrazine-modified protein in EXAMPLE 12. Analysis by PAGE gel demonstrated similar efficiency as conjugation as observed in EXAMPLE 12.

EXAMPLE 15

Preparation of a Hydrazide Modified Protein

A 5 mg/mL solution of ovalbumin in PBS (100 mM phosphate, 150 mM NaCl, pH 7.4) and 2 mM EDTA (200 μL; 1 mg protein) was prepared. A solution of succinimidyl 4-hydrazidoterephalate hydrochloride (SHTH)(2 mg) in DMF (50 μL) is prepared. To the protein solution was added the SHTH/DMF solution (15 eq.). The reaction mixture was incubated at room temperature for 4 hours. The modified protein was isolated and buffer exchanged by placing the reaction mixture in a 30 K ultra-free centrifugation device and washing three times with 0.1 M MES, 0.9% NaCl, pH 4.7 (3×400 μL). The purified protein was quantified for protein concentration (BOA assay; Pierce Chemical Co., Rockford, Ill.).

EXAMPLE 16

Conjugation of a Hydrazide-Modified Protein to an Aldehyde Modified Protein

The hydrazide-modified protein prepared in EXAMPLE 15 was reacted with aldehyde-modified protein in an identical manner as described for the hydrazine-modified protein in EXAMPLE 12. Analysis by PAGE gel demonstrated similar efficiency as conjugation as observed in EXAMPLE 12.

EXAMPLE 17

Preparation of BSA-$(NHNH_2)_n$/Oxidized Dextran Conjugate

To a solution of dextran (MW 5000; 0.20 mL; 10 mg/mL in PBS) was added a 100 mM solution of sodium periodate in water to give a final periodate concentration of 5 $\mu$M. The reaction mixture was incubated at room temperature for 20 min and subsequently concentrated in 0.5 mL ultrafree 5 K MWCO device. The retentate was washed with PBS (2×400 $\mu$L). The retentate was diluted to 200 $\mu$L with buffer and added to a solution of hydrazino-modified BSA (100 $\mu$L of a 2.5 mg/mL solution prepared as described above in EXAMPLE 9. PAGE gel analysis of the reaction mixture demonstrate complete conjugation of the protein to the oxidized dextran.

EXAMPLE 18

General Procedure for the Modification of Gold Particles with Succinimidyl Hydrazinium Modification Reagent To a solution of cysteamine (1 mmol; Aldrich Chemical Company, Milwaukee, Wis.) in DMF is added a solution of succinimidyl 6-BOC-hydrazinonicotinate (2 mmol) in DMF. The reaction mixture is stirred at room temperature until all ester has been consumed as determined by TLC (thin layer chromatography). The solvent is removed under reduced pressure and the product is isolated by silica gel chromatography.

To a suspension of gold particles (10 mg) in 0.1 M conjugation buffer, pH 7.4 is added a solution of the above compound (20 mg) in DMF (20 $\mu$L). The reaction mixture is stirred for 16 hours at room temperature and the supernatant is removed and the gold particles are washed with water three times. The particles are ready for capture of biomolecules modified with aldehydes.

EXAMPLE 19

Oxidation of Carbohydrate Moieties on Antibodies

To a solution of polyclonal or monoclonal antibody (100 $\mu$L; 5 mg/mL) in buffer (100 mM acetate or MES, pH 4.0–5.5) is added a solution of sodium periodate (5 $\mu$L of a 100 mM solution in water for a final periodate concentration of 5 $\mu$M). The reaction mixture is incubated at room temperature for 20 minutes and purified using an Ultrafree 30K or 50K MWCO device by initially concentrating the reaction mixture followed by two washes with buffer.

EXAMPLE 20

Conjugation of Hydrazine-modified IgG to Periodate-oxidized Horseradish Peroxidase To a solution of hydrazine-modified IgG prepared as described in EXAMPLE 11 was added to a solution of periodate-oxidized horseradish peroxidase (Pierce Chemical Co., Rockford, Ill.) and incubated at room temperature for 2 h. PAGE analysis of the reaction mixture deomonstrated >80% formation of conjugate.

EXAMPLE 21

Immobilization of oxidized Horseradish Peroxidase to Hydrazine-Modified Plates Periodate-oxidized horseradish peroxidase (Pierce Chemical Co., Rockford, Ill.) is diluted to the desired concentration and added to 96–3456 well plates that had been modified to possess hydrazino groups as described above in EXAMPLE 9. The antibody solution is allowed to incubate for 2–18 hours followed by removal of the solution and washing with 0.5% Tween® solution (twice) and buffer (twice).

EXAMPLE 22

Procedure for the Modification of a Synthetic Oligonucleotide Possessing a 5'-Amino Group with a Succinimidyl Protected Hydrazine Modification Reagent a. Preparation of a 5'-hydrazine-modified Oligonucleotide A 25-mer phosphodiester oligonucleotide modified to incorporate a C6-aminolinker (Glen Research amino-C6 amidite) was prepared (5'—$NH_2$—$(CH_2)_6$-ttt ttt tag cct aac tga tgc cat g-3'; MW 7791 g/mol, 229.5 OD/$\mu$mol; TriLink BioTechnologies, Inc., San Diego, Calif.). The oligonucleotide was dissolved in conjugation buffer (100 mM phosphate, 150 mM sodium chloride, pH 7.4) to a concentration of 0.92 OD/$\mu$L. To a solution of oligonucleotide (64 $\mu$L; 2 mg) was added DMF (32 $\mu$L). A solution of SANH (EXAMPLE 2; 3.8 mg) in DMF (100 $\mu$L) was prepared. An aliquot of the SANH/DMF solution (18.8 $\mu$L; 10 equivalents) was added to the oligonucleotide solution and the reaction allowed to incubate at room temperature overnight. The reaction was monitored by C18 RP-HPLC (solution A: 50 mM triethylammonium acetate, solution B: acetonitrile-gradient 0–50% A over 30 min; 50–80% over 10 min; 80–0% over 5 min). The hydrazine-modified oligonucletide was deprotected and purified using a Millipore 5K MWCO ultrafree diafiltration device by diluting the reaction mixture with 100 mM acetate, pH 4.7 and concentrating in the diafiltration device. The retentate was further washed with buffer (2×400 $\mu$L). The oligonucleotide was quantified by A260 assay and the hydrazine incorporation was determined using the p-nitrobenzaldehyde assay described in EXAMPLE 9.

b. Preparation of a 5'-aldehyde-modified Oligonucleotide

The protocol described above was followed using succinimidyl 4-formylbenzoate (Pierce Chemicals, Rockville, Ill.). The oligonucleotide was quantified by A260 assay and the aldehdye incorporation was determined using the 2-hydrazinopyridine 0.5 mM in acetate, pH 4.7 assay described in EXAMPLE 10 (A360, e 20,000).

EXAMPLE 23

Figure 5:
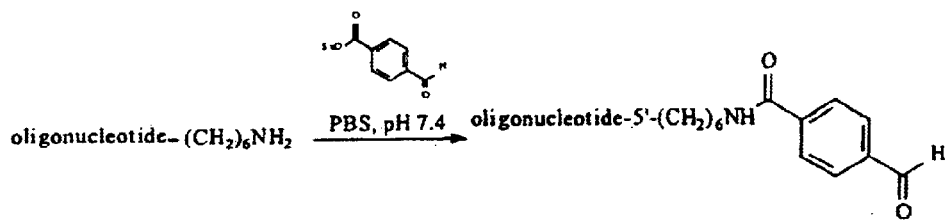
FIG. 5 is a scheme for the post-synthetic incorporation of aldehyde and hydrazine moieties on amino-modified oligonucleotides.
Figure 5:
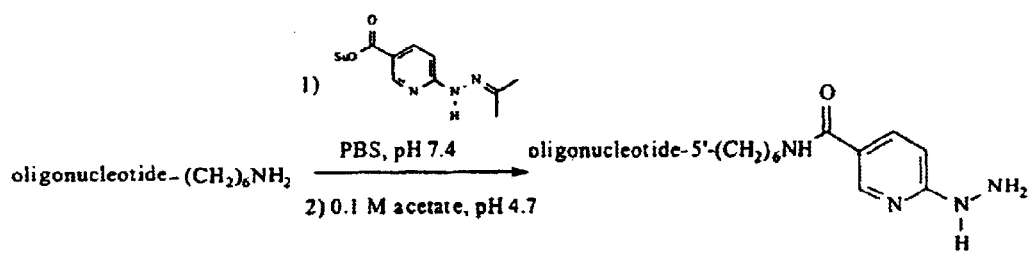
Figure 5:
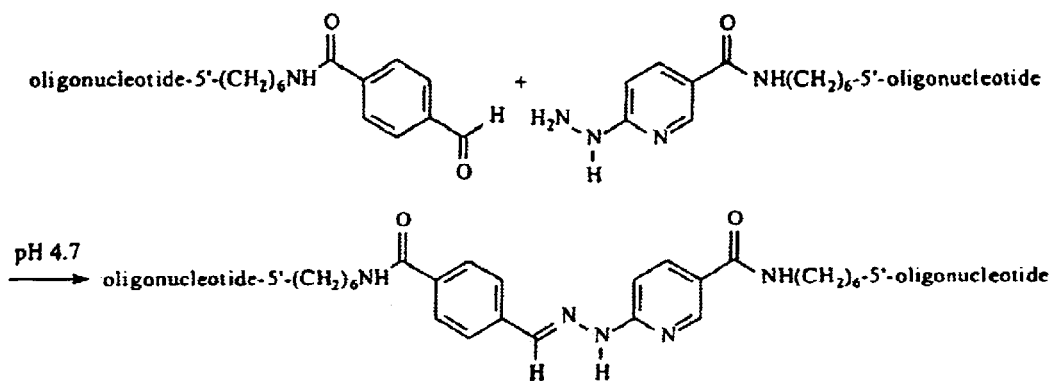

Crosslinking of a 5'-Hydrazino-Modified Oligonucleotide to a 5'-Aldehyde-Modified-Oligonucleotide As shown in FIG. 5, the crosslinking was performed by mixing the 5'-hydrazine oligonucleotide (EXAMPLE 22.a., 0.05 OD) with the 5'-aldehdye oligonucleotide (EXAMPLE 22.b., 0.2 OD) and incubating at room temperature for 16 h. The reaction was analyzed by PAGE (15% acrylamide gel) by comparing starting reagents and reaction product in separate lanes. The results indicated that a new band with lower mobility in the gel was present where the dimer product is expected.

EXAMPLE 24

Preparation of Aliphatic Succinimidyl Oxyamino Hydrochloride

Succinimidyl BOC-aminooxyacetate (Kaneko et al. (1991) *Bioconjugate Chem.* 1:133; 1 equiv) is added to 4M HCl/dioxane (Aldrich Chemical Co., Milwaukee, Wis.) and stirred at room temperature overnight. The solids that formed are isolated by centrifugation and repeatedly (three times) washed with dry dioxane to give the desired succinimidyl ester hydrochloride.

EXAMPLE 25

Preparation of Succinimidyl Aliphatic Oxime

To a solution of aminooxyacetic acid (1 equiv) in dioxane is added acetone (1.2 equiv) and the reaction mixture stirred at room temperature for 1 h. To the reaction mixture is added N-hydroxysuccinimide (1 equiv.) followed by the addition of a dropwise solution of DCC (1 equiv) in dioxane. The reaction mixture is stirred at room temperature for 4 hours. The precipitated DCU is removed by filtration and the filtrate is concentrated to dryness yielding the desired succinimidyl ester oxime.

EXAMPLE 26

Preparation of a Bifunctional Aromatic Oxyammonium Hydrochloride, —O— Oxyammoniumnicotinate Hydrochloride (SONH)

Figure 9:
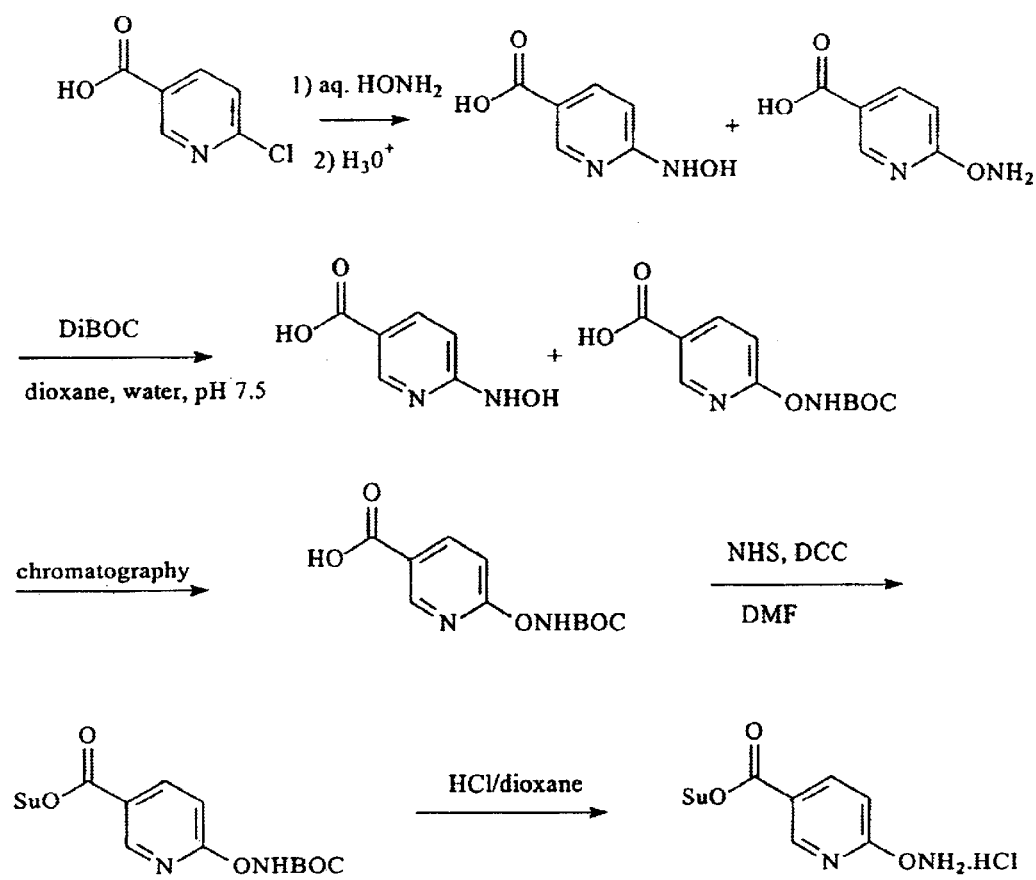
FIG. 9 is a synthetic scheme for synthesis of an aminooxy crosslinking reagent provided herein.

As shown in FIG. 9, to a solution of 6-chloronicotinic acid (1 equivalent) in 80% aqueous ethanol is added hydroxylamine (500 equivalents) and the solution is refluxed for 16 hours. The reaction mixture is concentrated to dryness and dissolved in water. The solution cooled in an ice bath and acidified with concentrated hydrochloric acid until a precipitate forms, pH approximately 5.0. The solids are isolated, redissolved in water and the pH of the solution raised to 7.5 with base. Dioxane (1 volume) is added to the solution followed by the dropwise addition of di-t-butyl dicarbonate (5 equivalents; Aldrich Chemical Co.). The reaction mixture is stirred at room temperature for 4 hours and the dioxane removed on the rotavap. The residue is chromatographed on silica to isolate the desired BOC acid. The acid (1 equiv) is dissolved in DMF and treated with NHS (1 equiv) followed by the dropwise addition of DCC (1 equiv) in DMF. The reaction mixture is stirred at room temperature for 4 hours and the solids removed by filtration and the filtrate concentrated to dryness and resuspended in ethyl acetate. Further precipitate is removed by filtration and the filtrate concentrated to dryness and the desired BOC succinimidyl ester is isolated by silica gel chromatography.

The BOC succinimidyl ester is dissolved in dioxane and treated with an equal volume of 4 N HCl/dioxane (Aldrich Chemical Co.) and the reaction mixture stirred at room temperature overnight. The precipated product that formed is isolated by removing excess HCl by bubbling Ar through the reaction mixture followed by centrifugation of the heterogeneous mixture. The supernatant is discarded and the pellet is washed repeatedly with dioxane. The final solid is dried under reduced pressure to give the desired product succinimidyl 6-O-oxyammoniumnicotinate hydrochloride (SONH).

EXAMPLE 27

Preparation of an Oxyamino-Modified Protein

A 5 mg/mL solution of ovalbumin in PBS (100 mM phosphate, 150 mM NaCl, pH 7.4) and 2 mM EDTA (200 μL; 1 mg protein) is prepared. A solution of succinimidyl aminooxyacetate hydrochloride (SAAH)(2 mg) in DMF (50 μL) is prepared. To the protein solution is added the SAAH/DMF solution (15 eq.). The reaction mixture is incubated at room temperature for 4 hours. The modified protein is isolated and buffer exchanged by placing the reaction mixture in a 30K ultra-free centrifugation device and washing three times with 0.1 M MES, 0.9% NaCl, pH 4.7 (3×400 pL). The purified protein is quantified for protein concentration (BCA assay; Pierce Chemical Co., Rockford, Ill.).

EXAMPLE 28

Preparation of a Hydrazinonicotinamide Modified Polymer A solution of poly-1-lysine (10 mg; Sigma Chemicals, St. Louis, Mo.; cat. #P-7890) was dissolved in conjugation buffer, 0.1 M phosphate, 0.15 M NaCl, pH 7.4 (1 mL). A solution of succinimidyl 6-hydrazinonicotinate acetone hydrazone (SANH; 1.3 mg) was dissolved in DM50 (13 μL). To two poly-1-lysine aliquots (200 μL) were added the SANHIDMSO solution (2.85 μL (10 equivalents) and 5.7 μL (20 equivalents)). The reaction mixtures were vortexed and incubated at room temperature for 2 h. The modified polymer was isolated by gel filtration on a NAP-25 column (Pharmacia) pre-equilibrated with 0.1 M MES, 0.9% NaCl, pH 4.7 buffer. Fractions (1 mL) were collected and analyzed by UV (A260). Fractions containing UV active product were combined to yield the desired product. The product was analyzed colorimetrically for hydrazine content by dissolving an aliquot (2 μL) in a 0.5 mM solution of p-nitrobenzaldehyde (98 μL) and incubating at 37° C. for 1 h followed by taking A390 readings (extinction coefficient 22000). The HyNic:poly-1-lysine polymer was used directly in the conjugation step. The amine/hydrazine content was determined using the TNBSA assay (trinitrobenzenesulfonic acid; Pierce Chemical, Inc., Rockville, Ill.).

EXAMPLE 29

Preparation of a Aliphatic Hydrazine Modified Protein and Conjugation to Periodate Oxidized Bacterial Polysaccharide A solution of a bacterial polysaccharide that possesses unsaturation in its lipids (from ATCC; 10 mg/mL) in water is treated with 10 mM sodium periodate (1/10 volume to make the solution 1 mM in periodate) and incubated at room temperature for 30 mm. The reaction mixture is passed through a sephadex G-25 column pre-equilibrated with water to remove small molecule impurities. The polysaccharide combining fractions are combined and concentrated to 5 mg/mL. SAAH (see Example 27) and to the oxyamino-modified protein in MES is added the oxidized bacterial polysaccharide. The reaction mixture is incubated at room temperature for 4 hours and the conjugate isolated by size exclusion chromatography on a Superdex 200 column (AP Biotech, Piscataway, N.J.).

Since modifications will be apparent to those of skill in this art, it is intended that this invention be limited only by the scope of the appended claims.

What is claimed is:

1. A compound of formula 1

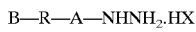

wherein;

A is —NHC(=S)—;
B is an amino reactive moiety;
R is —OOC— ($C_6H_{10}$) —$CH_2$—; and
X is a negative counterion.

2. The compound according to claim 1, wherein X is a halide or trifluoroacetate.

3. The compound according to claim 1, wherein B is an amino reactive moiety which is a succinimidyl ester, a hydroxybenzotriazolyl ester or a pentafluorophenol ester.

4. A conjugate comprising the compound according to claim 1, bound to a biological molecule.

5. The conjugate according to claim 4, wherein the biological molecule is a protein, a glycoprotein, or a peptide.

6. The conjugate according to claim 4, wherein the biological molecule is a polynucleotide, an oligonucleotide, an RNA or a DNA.

7. The conjugate according to claim 5, wherein the protein is an antibody.

8. A method of immobilizing a biological molecule, comprising:

(a) preparing the conjugate according to claim 4; and
(b) applying the conjugate to a surface wherein the surface has at least one carbonyl moiety for a time and under conditions such that the hydrazine moiety of the conjugate reacts with the at least one carbonyl moiety of the surface forming a hydrazone bond to the surface.

9. A method of immobilizing a biological molecule, comprising:

(a) applying the compound according to claim 1 to a surface comprising at least one amine moiety; and
(b) applying a biological molecule having at least one carbonyl moiety for a time and under conditions such that the hydrazine moiety of the surface reacts with the at least one carbonyl moiety of the biological molecule forming a hydrazone bond to the surface.

10. A method of crosslinking a first biological molecule to a second biological molecule, comprising:

(a) preparing the conjugate of the first biological molecule according to claim 4; and
(b) mixing the conjugate with the second biological molecule wherein the second biological molecule has at least one carbonyl moiety for a time and under conditions such that the hydrazine moiety of the conjugate reacts with the at least one carbonyl moiety of the second biological molecule forming a hydrazone bond crosslinking the first biological molecule to the second biological molecule.

11. The method according to claim 10 wherein the first biological molecule is a protein, a glycoprotein, or a peptide.

12. The method according to claim 10, wherein the first biological molecule is a polynucleotide, an oligonucleotide, an RNA or a DNA.

13. The method according to claim 11, wherein the protein is an antibody.

14. The compound according to claim 1 of the formula:

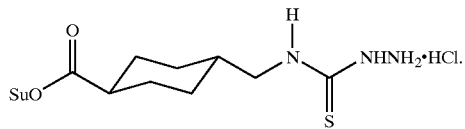

* * * * *